(12) United States Patent
Braca

(10) Patent No.: US 11,987,604 B2
(45) Date of Patent: May 21, 2024

(54) FUSION-PROTEINS BASED ON HUMAN FERRITIN AND PROTEASE-CLEAVABLE PEPTIDES AND THEIR USE AS CHEMOTHERAPEUTICS CARRIERS

(71) Applicant: THENA BIOTECH S.R.L., Latina (IT)

(72) Inventor: Aldo Braca, Latina (IT)

(73) Assignee: THENA BIOTECH S.R.L., Latina (IT)

( * ) Notice: Subject to any disclaimer, the term of this patent is extended or adjusted under 35 U.S.C. 154(b) by 310 days.

(21) Appl. No.: 16/761,303

(22) PCT Filed: Nov. 5, 2018

(86) PCT No.: PCT/IB2018/058655
§ 371 (c)(1),
(2) Date: May 4, 2020

(87) PCT Pub. No.: WO2019/087155
PCT Pub. Date: May 9, 2019

(65) Prior Publication Data
US 2021/0403515 A1    Dec. 30, 2021

(30) Foreign Application Priority Data
Nov. 6, 2017 (IT) .......... 102017000116184

(51) Int. Cl.
| C07K 14/47 | (2006.01) |
| A61K 9/51 | (2006.01) |
| A61K 47/64 | (2017.01) |
| A61K 47/69 | (2017.01) |
| A61P 35/00 | (2006.01) |

(52) U.S. Cl.
CPC .......... C07K 14/47 (2013.01); A61K 9/51 (2013.01); A61K 47/64 (2017.08); A61K 47/6925 (2017.08); A61P 35/00 (2018.01); C07K 2319/31 (2013.01); C07K 2319/33 (2013.01); C07K 2319/50 (2013.01)

(58) Field of Classification Search
CPC . A61K 9/00; A61K 9/51; A61K 47/00; A61K 47/64; A61K 47/6925; C07K 14/47; C07K 2319/31; C07K 2319/50; C07K 2319/735; C07K 2319/33; B82Y 5/00; A61P 35/00

USPC .......... 424/1.11, 1.29, 1.37, 1.65, 1.81, 1.85, 424/1.89, 9.1, 9.2, 9.6; 530/300
See application file for complete search history.

(56) References Cited

U.S. PATENT DOCUMENTS 10,640,775 B2 *    5/2020    Ceci ............... A61K 39/001159

FOREIGN PATENT DOCUMENTS

| WO | WO-2008155134 A1 | 12/2008 | |
| WO | WO-2016051340 A1 * | 4/2016 | ......... A61K 39/0011 |
| WO | WO-2019087155 A1 | 5/2019 | |

OTHER PUBLICATIONS

Fracasso et al, Journal of Controlled Release, vol. 239, pp. 10-18 (Year: 2016).*
Falvo et al, Biomacromolecules, vol. 17, pp. 514-522 (Year: 2016).*
Falvo et al, Journal of Controlled Release, vol. 275, pp. 177-185 (Year: 2018).*
Giulio, F., et al., "Selective Delivery of doxorubicin by novel stimuli-sensitive nano-ferritins overcomes tumor refractoriness," Journal of Controlled Release 239:10-18, Elsevier, Netherlands (2016).
International Search Report and Written Opinion dated Dec. 10, 2018 for International Application No. PCT/IB2018/058655, European Patent Office, Netherlands, 10 pages.

* cited by examiner

Primary Examiner — D. L. Jones
(74) Attorney, Agent, or Firm — Sterne, Kessler, Goldstein & Fox P.L.L.C.

(57) ABSTRACT

A fusion protein, a nanoparticle composed by a plurality of monomers of said fusion protein, and uses thereof. A fusion protein based on the heavy chain of human ferritin is de-scribed, which includes at the N terminus of the protein at least one metalloproteinase cleavage sequence and a modified PAS polypeptide that acts as a masking polymer that in-creases the protein drug stability, as well as a nanoparticle composed of multiple monomers of said fusion protein, a nucleic acid encoding for said fusion protein, and diagnostic and therapeutic applications thereof.

13 Claims, 16 Drawing Sheets

Specification includes a Sequence Listing.

| Protein | MITOXANTRONE (MIT) | | PIXANTRONE (PIX) | |
| --- | --- | --- | --- | --- |
| | Protein recovery (%) | Number of MIT molecules per 24-mer | Protein recovery (%) | Number of PIX molecules per 24-mer |
| HFt-MP-PAS | 60±4 | 55±4 | 54±5 | 25±4 |
| HFt-MP-PASE | 90±3 | 49±5 | 91±4 | 28±3 |
| HFt | 19±3 | 48±4 | 20±4 | 21±4 |

FIG 4

| Cancer cells | IC$_{50}$ (μM) Free MIT | IC$_{50}$ (μM) HFt-MP-PASE-MIT |
| --- | --- | --- |
| SW480 | 0.005 ± 0.001 | 0.004 ± 0.001 |
| SW620 | 0.004 ± 0.001 | 0.005 ± 0.001 |
| MDA-MB-231 | 0.03 ± 0.009 | 0.02 ± 0.007 |
| HT1080 | 0.01 ± 0.008 | 0.009 ± 0.005 |
| PaCa44 | 0.43 ± 0.12 | 0.43 ± 0.34 |
| Capan-1 | 0.72 ± 0.23 | 0.10 ± 0.04 |
| MiaPaCa2 | 0.11 ± 0.06 | 0.07 ± 0.02 |

FIG 9

| Protein | Protein recovery (%) | Number of drug molecules conjugated per 24-mer |
|---|---|---|
| HFt-Cys2-MP-PASE | 92±3 | 69±4 (DOX-EMCH) |
| HFt-Cys1-MP-PASE | 91±3 | 74±5 (maleimido-propionic acid + Genz 644282) |
| HFt-MP-PASE | 90±3 | 49±5 (Mitoxantrone) |
| HFt-Glu-MP-PASE | 91±3 | 70±5 (Mitoxantrone) |
| HFt-MP-PASE | 75±4 | 24±3 (Genz 644282) |
| HFt-Glu-MP-PASE | 90±4 | 80±4 (Genz 644282) |

FIG 13

| Cancer cells | IC$_{50}$ (nM) Free Genz-644282 | IC$_{50}$ (nM) HFt-Glu-MP-PASE-Genz |
|---|---|---|
| A204 | 5.8 ± 0.41 | 4.44 ± 0.33 |
| Colo38 | 6.99 ± 0.01 | 5.85 ± 0.03 |
| MDA-MB-231 | 19.03 ± 2.6 | 20.1 ± 1.7 |
| HT1080 | 5.41 ± 0.8 | 4.09 ± 0.5 |
| PaCa44 | 150.4 ± 30.6 | 100.4 ± 19.3 |
| MiaPaCa2 | 26.1 ± 2.6 | 14.5 ± 1.6 |

FIG 14

SEQUENCE LISTING

```
<160> NUMBER OF SEQ ID NOS: 18

<210> SEQ ID NO 1
<211> LENGTH: 183
<212> TYPE: PRT
<213> ORGANISM: Artificial Sequence
<220> FEATURE:
<223> OTHER INFORMATION: Human Ferritin Heavy Chain

<400> SEQUENCE: 1
```

Met Thr Thr Ala Ser Thr Ser Gln Val Arg Gln Asn Tyr His Gln Asp
1               5                   10                  15

Ser Glu Ala Ala Ile Asn Arg Gln Ile Asn Leu Glu Leu Tyr Ala Ser
            20                  25                  30

Tyr Val Tyr Leu Ser Met Ser Tyr Tyr Phe Asp Arg Asp Asp Val Ala
        35                  40                  45

Leu Lys Asn Phe Ala Lys Tyr Phe Leu His Gln Ser His Glu Glu Arg
    50                  55                  60

Glu His Ala Glu Lys Leu Met Lys Leu Gln Asn Gln Arg Gly Gly Arg
65                  70                  75                  80

Ile Phe Leu Gln Asp Ile Lys Lys Pro Asp Cys Asp Asp Trp Glu Ser
                85                  90                  95

Gly Leu Asn Ala Met Glu Cys Ala Leu His Leu Glu Lys Asn Val Asn
            100                 105                 110

Gln Ser Leu Leu Glu Leu His Lys Leu Ala Thr Asp Lys Asn Asp Pro
        115                 120                 125

```
His Leu Cys Asp Phe Ile Glu Thr His Tyr Leu Asn Glu Gln Val Lys
    130                 135                 140

Ala Ile Lys Glu Leu Gly Asp His Val Thr Asn Leu Arg Lys Met Gly
145                 150                 155                 160

Ala Pro Glu Ser Gly Leu Ala Glu Tyr Leu Phe Asp Lys His Thr Leu
                165                 170                 175

Gly Asp Ser Asp Asn Glu Ser
            180

<210> SEQ ID NO 2
<211> LENGTH: 183
<212> TYPE: PRT
<213> ORGANISM: Artificial Sequence
<220> FEATURE:
<223> OTHER INFORMATION: HFt Cys1

<400> SEQUENCE: 2

Met Thr Thr Ala Ser Thr Ser Gln Val Arg Gln Asn Tyr His Gln Asp
1               5                   10                  15

Ser Glu Ala Ala Ile Asn Arg Gln Ile Asn Leu Glu Leu Tyr Ala Ser
                20                  25                  30

Tyr Val Tyr Leu Ser Met Ser Tyr Tyr Phe Asp Arg Asp Asp Val Ala
            35                  40                  45

Leu Lys Asn Phe Ala Lys Tyr Phe Leu His Gln Ser His Glu Glu Arg
 50                  55                  60

Glu His Ala Glu Lys Leu Met Cys Leu Gln Asn Gln Arg Gly Gly Arg
65                  70                  75                  80

Ile Phe Leu Gln Asp Ile Lys Lys Pro Asp Ser Asp Asp Trp Glu Ser
                85                  90                  95

Gly Leu Asn Ala Met Glu Ser Ala Leu His Leu Glu Lys Asn Val Asn
            100                 105                 110

Gln Ser Leu Leu Glu Leu His Lys Leu Ala Thr Asp Lys Asn Asp Pro
        115                 120                 125

His Leu Ser Asp Phe Ile Glu Thr His Tyr Leu Asn Glu Gln Val Cys
    130                 135                 140

Ala Ile Lys Glu Leu Gly Asp His Val Thr Asn Leu Arg Lys Met Gly
145                 150                 155                 160

Ala Pro Glu Ser Gly Leu Ala Glu Tyr Leu Phe Asp Lys His Thr Leu
                165                 170                 175

Gly Asp Ser Asp Asn Glu Cys
            180

<210> SEQ ID NO 3
<211> LENGTH: 8
<212> TYPE: PRT
<213> ORGANISM: Artificial Sequence
<220> FEATURE:
<223> OTHER INFORMATION: fusion protein domain

<400> SEQUENCE: 3

Gly Pro Leu Gly Ile Ala Gly Gln
1               5

<210> SEQ ID NO 4
<211> LENGTH: 8
<212> TYPE: PRT
<213> ORGANISM: Artificial Sequence
<220> FEATURE:
<223> OTHER INFORMATION: fusion protein domain
```

```
<400> SEQUENCE: 4

Gly Pro Gln Gly Ile Trp Gly Gln
1               5

<210> SEQ ID NO 5
<211> LENGTH: 6
<212> TYPE: PRT
<213> ORGANISM: Artificial Sequence
<220> FEATURE:
<223> OTHER INFORMATION: fusion protein domain

<400> SEQUENCE: 5

Pro Leu Gly Leu Ala Gly
1               5

<210> SEQ ID NO 6
<211> LENGTH: 6
<212> TYPE: PRT
<213> ORGANISM: Artificial Sequence
<220> FEATURE:
<223> OTHER INFORMATION: fusion protein domain

<400> SEQUENCE: 6

Pro Val Gly Leu Ile Gly
1               5

<210> SEQ ID NO 7
<211> LENGTH: 5
<212> TYPE: PRT
<213> ORGANISM: Artificial Sequence
<220> FEATURE:
<223> OTHER INFORMATION: fusion protein domain

<400> SEQUENCE: 7

Cys Gly Leu Asp Asp
1               5

<210> SEQ ID NO 8
<211> LENGTH: 16
<212> TYPE: PRT
<213> ORGANISM: Artificial Sequence
<220> FEATURE:
<223> OTHER INFORMATION: cleavage site protein

<400> SEQUENCE: 8

Gly Pro Leu Gly Ile Ala Gly Gln Gly Pro Leu Gly Ile Ala Gly Gln
1               5                   10                  15

<210> SEQ ID NO 9
<211> LENGTH: 42
<212> TYPE: PRT
<213> ORGANISM: Artificial Sequence
<220> FEATURE:
<223> OTHER INFORMATION: PASE rich peptide

<400> SEQUENCE: 9

Ala Ser Pro Ala Ala Pro Ala Pro Ala Ser Pro Ala Ala Pro Ala Pro
1               5                   10                  15

Ser Ala Pro Ala Glu Ala Ser Pro Ala Ala Pro Ala Pro Ala Ser Pro
            20                  25                  30

Ala Ala Pro Ala Pro Ser Ala Pro Ala Glu
        35                  40

<210> SEQ ID NO 10
<211> LENGTH: 40
```

```
<212> TYPE: PRT
<213> ORGANISM: Artificial Sequence
<220> FEATURE:
<223> OTHER INFORMATION: PASE rich peptide

<400> SEQUENCE: 10

Ala Ser Pro Ala Ala Pro Ala Pro Ala Ser Pro Ala Glu Pro Ala Pro
1               5                   10                  15

Ser Ala Pro Ala Ala Ser Pro Ala Ala Pro Ala Pro Ala Ser Pro Ala
                20                  25                  30

Glu Pro Ala Pro Ser Ala Pro Ala
                35                  40

<210> SEQ ID NO 11
<211> LENGTH: 73
<212> TYPE: PRT
<213> ORGANISM: Artificial Sequence
<220> FEATURE:
<223> OTHER INFORMATION: PASE rich peptide

<400> SEQUENCE: 11

Ala Ser Pro Ala Ala Pro Ala Pro Ala Ser Pro Ala Ala Pro Ala Pro
1               5                   10                  15

Ser Ala Pro Ala Glu Ala Ser Pro Ala Ala Pro Ala Pro Ala Ser Pro
                20                  25                  30

Ala Ala Pro Ala Pro Ser Ala Pro Ala Glu Ala Ser Pro Ala Ala Pro
                35                  40                  45

Ala Pro Ala Ser Pro Ala Ala Pro Ala Pro Ser Ala Pro Ala Glu Ala
                50                  55                  60

Ser Pro Ala Ala Pro Ala Pro Ala Ser
65                  70

<210> SEQ ID NO 12
<211> LENGTH: 42
<212> TYPE: PRT
<213> ORGANISM: Artificial Sequence
<220> FEATURE:
<223> OTHER INFORMATION: PASE rich peptide

<400> SEQUENCE: 12

Ala Ser Pro Ala Ala Pro Ala Pro Ala Ser Pro Ala Ala Pro Ala Pro
1               5                   10                  15

Ser Ala Pro Ala Asp Ala Ser Pro Ala Ala Pro Ala Pro Ala Ser Pro
                20                  25                  30

Ala Ala Pro Ala Pro Ser Ala Pro Ala Asp
                35                  40

<210> SEQ ID NO 13
<211> LENGTH: 40
<212> TYPE: PRT
<213> ORGANISM: Artificial Sequence
<220> FEATURE:
<223> OTHER INFORMATION: PASE rich peptide

<400> SEQUENCE: 13

Ala Ser Pro Ala Ala Pro Ala Pro Ala Ser Pro Ala Asp Pro Ala Pro
1               5                   10                  15

Ser Ala Pro Ala Ala Ser Pro Ala Ala Pro Ala Pro Ala Ser Pro Ala
                20                  25                  30

Asp Pro Ala Pro Ser Ala Pro Ala
                35                  40
```

<210> SEQ ID NO 14
<211> LENGTH: 73
<212> TYPE: PRT
<213> ORGANISM: Artificial Sequence
<220> FEATURE:
<223> OTHER INFORMATION: PASE rich peptide

<400> SEQUENCE: 14

```
Ala Ser Pro Ala Ala Pro Ala Pro Ala Ser Pro Ala Ala Pro Ala Pro
1               5                   10                  15

Ser Ala Pro Ala Asp Ala Ser Pro Ala Ala Pro Ala Pro Ala Ser Pro
                20                  25                  30

Ala Ala Pro Ala Pro Ser Ala Pro Ala Asp Ala Ser Pro Ala Ala Pro
                35                  40                  45

Ala Pro Ala Ser Pro Ala Ala Pro Ala Pro Ser Ala Pro Ala Asp Ala
            50                  55                  60

Ser Pro Ala Ala Pro Ala Pro Ala Ser
65                  70
```

<210> SEQ ID NO 15
<211> LENGTH: 183
<212> TYPE: PRT
<213> ORGANISM: Artificial Sequence
<220> FEATURE:
<223> OTHER INFORMATION: Variant HFt Cys2

<400> SEQUENCE: 15

```
Met Thr Thr Ala Ser Thr Ser Gln Val Arg Gln Asn Tyr His Gln Asp
1               5                   10                  15

Ser Glu Ala Ala Ile Asn Arg Gln Ile Asn Leu Glu Leu Tyr Ala Ser
                20                  25                  30

Tyr Val Tyr Leu Ser Met Ser Tyr Tyr Phe Asp Arg Asp Asp Val Ala
            35                  40                  45

Leu Lys Asn Phe Ala Cys Tyr Phe Leu His Gln Ser His Glu Glu Arg
        50                  55                  60

Glu His Ala Glu Lys Leu Met Cys Leu Gln Asn Gln Arg Gly Gly Arg
65                  70                  75                  80

Ile Phe Leu Gln Asp Ile Lys Lys Pro Asp Ser Asp Trp Glu Ser
                85                  90                  95

Gly Leu Asn Ala Met Glu Ser Ala Leu His Leu Glu Lys Asn Val Asn
                100                 105                 110

Gln Ser Leu Leu Glu Leu His Lys Leu Ala Thr Asp Lys Asn Asp Pro
            115                 120                 125

His Leu Ser Asp Phe Ile Glu Cys His Tyr Leu Asn Glu Gln Val Cys
        130                 135                 140

Ala Ile Lys Glu Leu Gly Asp His Val Thr Asn Leu Arg Lys Met Gly
145                 150                 155                 160

Ala Pro Glu Ser Gly Leu Ala Glu Tyr Leu Phe Asp Lys His Thr Leu
                165                 170                 175

Gly Asp Ser Asp Asn Glu Ser
            180
```

<210> SEQ ID NO 16
<211> LENGTH: 229
<212> TYPE: PRT
<213> ORGANISM: Artificial Sequence
<220> FEATURE:
<223> OTHER INFORMATION: PAS matrix metalloproteinase HFt

<400> SEQUENCE: 16

```
Met Thr Thr Ala Ser Thr Ser Gln Val Arg Gln Asn Tyr His Gln Asp
1               5                   10                  15

Ser Glu Ala Ala Ile Asn Arg Gln Ile Asn Leu Glu Leu Tyr Ala Ser
                20                  25                  30

Tyr Val Tyr Leu Ser Met Ser Tyr Tyr Phe Asp Arg Asp Asp Val Ala
            35                  40                  45

Leu Lys Asn Phe Ala Lys Tyr Phe Leu His Gln Ser His Glu Glu Arg
        50                  55                  60

Glu His Ala Glu Lys Leu Met Lys Leu Gln Asn Gln Arg Gly Gly Arg
65                  70                  75                  80

Ile Phe Leu Gln Asp Ile Lys Lys Pro Asp Cys Asp Asp Trp Glu Ser
                85                  90                  95

Gly Leu Asn Ala Met Glu Cys Ala Leu His Leu Glu Lys Asn Val Asn
            100                 105                 110

Gln Ser Leu Leu Glu Leu His Lys Leu Ala Thr Asp Lys Asn Asp Pro
        115                 120                 125

His Leu Cys Asp Phe Ile Glu Thr His Tyr Leu Asn Glu Gln Val Lys
    130                 135                 140

Ala Ile Lys Glu Leu Gly Asp His Val Thr Asn Leu Arg Lys Met Gly
145                 150                 155                 160

Ala Pro Glu Ser Gly Leu Ala Glu Tyr Leu Phe Asp Lys His Thr Leu
                165                 170                 175

Gly Asp Ser Asp Asn Glu Ser Pro Leu Gly Leu Ala Gly Ala Ser Pro
            180                 185                 190

Ala Ala Pro Ala Pro Ala Ser Pro Ala Ala Pro Ala Pro Ser Ala Pro
        195                 200                 205

Ala Ala Ser Pro Ala Ala Pro Ala Pro Ala Ser Pro Ala Ala Pro Ala
        210                 215                 220

Pro Ser Ala Pro Ala
225
```

<210> SEQ ID NO 17
<211> LENGTH: 229
<212> TYPE: PRT
<213> ORGANISM: Artificial Sequence
<220> FEATURE:
<223> OTHER INFORMATION: PASE matrix metalloproteinase HFT

<400> SEQUENCE: 17

```
Met Thr Thr Ala Ser Thr Ser Gln Val Arg Gln Asn Tyr His Gln Asp
1               5                   10                  15

Ser Glu Ala Ala Ile Asn Arg Gln Ile Asn Leu Glu Leu Tyr Ala Ser
                20                  25                  30

Tyr Val Tyr Leu Ser Met Ser Tyr Tyr Phe Asp Arg Asp Asp Val Ala
            35                  40                  45

Leu Lys Asn Phe Ala Lys Tyr Phe Leu His Gln Ser His Glu Glu Arg
        50                  55                  60

Glu His Ala Glu Lys Leu Met Lys Leu Gln Asn Gln Arg Gly Gly Arg
65                  70                  75                  80

Ile Phe Leu Gln Asp Ile Lys Lys Pro Asp Cys Asp Asp Trp Glu Ser
                85                  90                  95

Gly Leu Asn Ala Met Glu Cys Ala Leu His Leu Glu Lys Asn Val Asn
            100                 105                 110

Gln Ser Leu Leu Glu Leu His Lys Leu Ala Thr Asp Lys Asn Asp Pro
```

```
            115                 120                 125
His Leu Cys Asp Phe Ile Glu Thr His Tyr Leu Asn Glu Gln Val Lys
    130                 135                 140

Ala Ile Lys Glu Leu Gly Asp His Val Thr Asn Leu Arg Lys Met Gly
145                 150                 155                 160

Ala Pro Glu Ser Gly Leu Ala Glu Tyr Leu Phe Asp Lys His Thr Leu
                165                 170                 175

Gly Asp Ser Asp Asn Glu Ser Pro Leu Gly Leu Ala Gly Ala Ser Pro
            180                 185                 190

Ala Ala Pro Ala Pro Ala Ser Pro Ala Glu Pro Ala Pro Ser Ala Pro
        195                 200                 205

Ala Ala Ser Pro Ala Ala Pro Ala Pro Ala Ser Pro Ala Glu Pro Ala
    210                 215                 220

Pro Ser Ala Pro Ala
225

<210> SEQ ID NO 18
<211> LENGTH: 183
<212> TYPE: PRT
<213> ORGANISM: Artificial Sequence
<220> FEATURE:
<223> OTHER INFORMATION: HFt Glu Variant

<400> SEQUENCE: 18

Met Thr Thr Ala Ser Thr Ser Gln Val Arg Gln Asn Tyr His Gln Asp
1               5                   10                  15

Ser Glu Ala Ala Ile Asn Arg Gln Ile Asn Leu Glu Leu Tyr Ala Ser
                20                  25                  30

Tyr Val Tyr Leu Ser Met Ser Tyr Tyr Phe Asp Arg Asp Asp Val Ala
            35                  40                  45

Leu Lys Asn Phe Ala Glu Tyr Phe Leu His Gln Ser His Glu Glu Arg
    50                  55                  60

Glu His Ala Glu Lys Leu Met Glu Leu Gln Asn Gln Arg Gly Gly Arg
65                  70                  75                  80

Ile Phe Leu Gln Asp Ile Lys Lys Pro Asp Ser Asp Asp Trp Glu Ser
                85                  90                  95

Gly Leu Asn Ala Met Glu Ser Ala Leu His Leu Glu Lys Asn Val Asn
            100                 105                 110

Gln Ser Leu Leu Glu Leu His Lys Leu Ala Thr Asp Lys Asn Asp Pro
        115                 120                 125

His Leu Ser Asp Phe Ile Glu Glu His Tyr Leu Asn Glu Gln Val Glu
    130                 135                 140

Ala Ile Lys Glu Leu Gly Asp His Val Thr Asn Leu Arg Lys Met Gly
145                 150                 155                 160

Ala Pro Glu Ser Gly Leu Ala Glu Tyr Leu Phe Asp Lys His Thr Leu
                165                 170                 175

Gly Asp Ser Asp Asn Glu Ser
            180
```

FUSION-PROTEINS BASED ON HUMAN FERRITIN AND PROTEASE-CLEAVABLE PEPTIDES AND THEIR USE AS CHEMOTHERAPEUTICS CARRIERS

REFERENCE TO A SEQUENCE LISTING SUBMITTED ELECTRONICALLY VIA EFS-WEB

The content of the electronically submitted sequence listing in ASCII text file (Name: 4310.0020001_Seq-listing_ST25; Size: 15,684 bytes; and Date of Creation: Jan. 19, 2021) is herein incorporated by reference in its entirety.

TECHNICAL FIELD OF THE INVENTION

The present invention relates to a fusion protein, nanoparticles composed of a plurality of monomers of said fusion protein, nucleic acids encoding said fusion protein, and diagnostic and therapeutic applications thereof. The present invention relates to a fusion protein, a nanoparticle composed by a plurality of monomers of said fusion protein, and uses thereof. A fusion protein based on the heavy chain of human ferritin is described, which includes at the N terminus of the protein at least one metalloproteinase cleavage sequence and a modified PAS polypeptide that acts as a masking polymer that increases the protein-drug stability, as well as a nanoparticle composed of multiple monomers of said fusion protein, a nucleic acid encoding for said fusion protein, and diagnostic and therapeutic applications thereof.

State of Art

The selective release of therapeutic agents at diseased areas represents one of the most important challenges for improving the current therapies, especially in the anticancer therapy. In this context, the use of nanoparticles as carriers (nanovectors) of therapeutic agents potentially allows for both circumventing the biological barriers that may be present between the administration site and the final target and, more specifically, accumulating the drug in a selective way at the diseased area rather than in normal tissues. As a fundamental prerequisite, the nanovector must be able to bind large amounts of the drug in an effective way.

Among the known carriers for targeted drug release, nanoparticles based on ferritins (Fts) are becoming increasingly interesting thanks to their extraordinary characteristics of biocompatibility, ability of crossing biological barriers, functionalization versatility, and capability of binding certain types of drugs. Fts are highly symmetrical multimeric protein structures consisting of 24 subunits that assemble into a molecular structure with an essentially spherical shell, which encloses a cavity that is physiologically used for storing iron. The outer diameter and the inner diameter are 12 and 8 nm, respectively. Such a shell-shaped molecular structure will be hereinafter designated as "nanoparticle" or "HFt nanoparticle". Nanoparticles based on the heavy chain of human ferritin (HFt) show a number of advantages compared to other drug release systems, especially in connection with in vivo human applications. In fact, the HFt molecules are designed to cross the biological barriers (20 nm minor diameter) and are present both within cells and in blood under physiological conditions, although at low concentrations (approximately 20 µg/L).

Being natural elements, they are less likely to evoke a strong non-self (extraneous) antibody and/or T cell immune response. Furthermore, HFt is one of the few natural nanoparticles that is capable by itself of binding tumour cells in an effective and selective way. In fact, by using one of the most attractive molecules for targeted cancer therapy, transferrin receptor 1 (TfR1), it has been shown that HFt is internalized. TfR1 is indeed up-regulated at the surface of many types of cancer (up to 100 times higher than in normal cells) and is efficiently internalized. In more than 474 clinical tissue samples, HFt, but not the light chain of human ferritin (LFt), was proven to be internalized by TfR1 and to specifically recognize many types of tumours (i.e. liver, lung, pancreas, colon, cervix, ovary, prostate, breast, sarcoma, and thymus cancers) compared to non-tumour tissues, with 98% sensitivity and 95% specificity (Fan K, Cao C, Pan Y, Lu D, Yang D, Feng J, et al. Magnetoferritin nanoparticles for targeting and visualizing tumour tissues. Nat Nanotechnol. 2012; 7:459-64). However, native HFt exhibits a few disadvantages. Firstly, the yields with which it is capable of binding certain types of drugs, such as for example doxorubicin (one of the antineoplastic drugs with a broad anti-tumour spectrum) are low, and this may restrict their possible use and clinical development. Secondly, native HFt has a very short plasma half-life, approximately 2-3 hours, when injected through the systemic route. Lastly, its natural ferroxidase activity might inhibit the development and maturation of human osteoblasts, and bring about a decreased mineralization, osteopenia and osteoporosis (Zarjou A, Jeney V, Arosio P, Poli M, Zavaczki E, Balla G, Balla J. Ferritin ferroxidase activity: a potent inhibitor of osteogenesis. J Bone Miner Res. 2010, 25:164-72). For this reason, it is advisable to use an HFt variant lacking the ferroxidase activity, obtained by site-specific mutation (hereinafter designated as vHFt), which gives no inhibition.

Recently, to increase both the in vivo half-life of native HFt and the stability of HFt-drug complexes, a novel HFt-based construct, named HFt-MP-PAS, suitable for drug delivery was disclosed in WO2016051340 A1. In this construct the N-terminus of each HFt subunit is genetically fused to: i) a PAS polypeptide sequence, i.e., a sequence rich in proline (P), alanine (A) and serine (S) residues; and ii) a tumor-selective sequence (MP) responsive to proteolytic cleavage by tumor proteases (MMPs), inserted between each HFt subunit and the outer PAS polypeptide. The PAS shield was aimed at increasing the stability of the protein during the drug encapsulating process, preferably for the drug doxorubicin, and of increasing the stability of the protein-drug complex. The presence of PAS is also capable of masking the protein surface and thus of extending its plasma half-life. The MP sequence allows the PAS shield to be selectively removed by stimuli present in the tumor microenvironment (i.e., MMPs specific for this sequence) so that the resulting unmasked HFt can freely interact with and be internalized by TfR1 overexpressed in cancer cells. The HFt-MP-PAS construct proved to i) encapsulate in the internal cavity three times more doxorubicin (DOX) than wild-type HFt, ii) form more stable complexes (i.e., drug leakage was negligible) and iii) possess higher in vivo circulation time. Importantly, DOX-loaded HFt-MP-PAS (HFt-MP-PAS-DOX) displayed excellent therapeutic efficacy in a human pancreatic cancer model in vivo, significantly increasing overall animal survival. It was ascribed to the PAS shield the increase in DOX encapsulation, protein-drug complex stability and circulation time in plasma with respect to HFt. However, there is still a need to provide improved nanoparticles as carriers (nanovectors) of therapeutic agents.

SUMMARY OF THE INVENTION

The inventors surprisingly found that the insertion of at least one negatively charged residue selected from glutamate or aspartate in the PAS domain drastically improves the properties of the fusion protein HFt-MP-PAS as clearly showed from the experimental data reported in the examples and drawings of the present disclosure. In particular, the inventors unexpectedly found that the new construct with the insertion of a negatively charged residue such as glutamate in the PAS domain (HF-MP-PASE) outperforms both the native HFt and the HFt-MP-PAS proteins in terms of the amount of protein recovered at the end of the reactions for the encapsulation of the drug. Moreover, the new construct HF-MP-PASE showed a higher accumulation of the drug in the nuclei of the cells, a higher stability in serum and a higher tumor accumulation compared to the native HFt and the HFt-MP-PAS.

Accordingly, a first object of the present invention is a fusion protein, comprising at least three domains, wherein:
(a) a first domain comprises the amino acid sequence of the heavy of native human ferritin, or a variant thereof having at least 90% identity with the amino acid sequence of the heavy chain of native human ferritin;
(b) a second domain comprises the amino acid sequence of a matrix metalloproteinase (MMP) cleavage site; and
(c) a third N-terminal domain consists of the amino acid sequence of a polypeptide of at least 20 amino acid residues and which essentially consists or consists of proline, serine, alanine and at least one negatively charged residue selected from glutamate or aspartate.

The present invention provides also compositions comprising the compounds of the invention as well as for specific uses in therapeutic applications. This and other objects are accomplished through the fusion protein as defined in appended claim 1. The other independent claims and the dependent claims relate to further aspects and specific embodiments of the invention, which form an integral part of the specification.

The inventors to improve and facilitate drug binding within the ferritin cavity, decided to remove cysteine residues from the protein surface and to introduce additional cysteine residues in the protein cavity. In this way, it was possible to bind to the internal cavity every molecule containing a thiol-reactive motif, e.g drugs, linkers, fluorophores, etc, in a very effective manner (see examples and figures).

Accordingly, a further object of the present invention is a mutein of the heavy of native human ferritin wherein said mutein is without any residues of cysteine on the protein surface and with at least one cysteine in the internal cavity of the protein.

In addition, the inventors to improve and facilitate binding of positive drugs within the ferritin cavity, decided to remove cysteine residues from the protein surface and to introduce additional negatively charged residue selected from glutamate or aspartate, in the protein cavity. In this way, it was possible to bind to the internal cavity molecules containing positively charged motif, e.g drugs, linkers, fluorophores, etc, in a very effective manner (see examples and figures).

Accordingly, a further object of the present invention is a mutein of the heavy of native human ferritin wherein said mutein is without any residues of cysteine on the protein surface and with at least one extra glutamate or aspartate residue in the internal cavity of the protein.

A further object of the present invention is an isolated nucleic acid encoding for a fusion protein or a nanoparticle according to any one of embodiments herein disclosed.

A further object of the present invention is a vector comprising said nucleic acids and a host cell comprising said nucleic acid or said vector.

Further features and advantages of the invention will appear from the following detailed description, which is provided for illustrative purposes only and not by way of limitation, with reference to the appended drawings, wherein:

BRIEF DESCRIPTION OF THE DRAWINGS

FIG. 4 shows the ability to encapsulate mitoxantrone or pixantrone by the previous HFt construct (HFt-MP-PAS) compared to that of the novel HFt-MP-PASE protein and with other data from the literature. The relative yields are indicated in terms of % protein recovery and number of drug molecules bound. It can be seen that the construct subject matter of this patent surprisingly and unexpectedly has superior yields in terms of protein recovery compared both to the native HFt or modified HFt (HFt-MP-PAS).

FIG. 9 shows the killing efficacy of MIT and HFt-MP-PASE-MIT against human cell lines PaCa-44, Capan-1 and MiaPaCa2 (pancreatic carcinoma), HT1080 (fibrosarcoma), MDA-MB-231 (breast cancer) and SW480 and SW620 (colorectal cancer). Mean±S.E.M. (n=3)

FIG. 13 shows the ability to encapsulate a 6-maleimido-caproyl hydrazone derivative of Doxorubicin (DOX-EMCH) or the combination of maleimido-propionic acid and Genz 644282™ ([8,9-dimethoxy-5-(2-N-methylaminoethyl)-2,3-methylenedioxy-5H-dibenzo[c,h][1,6]naphthyridin-6-one]) by the novel HFt-Cys2-MP-PASE protein (containing 4 non-native cysteines per monomer, 96 per 24-mer) or the ability to encapsulate native mitoxantrone or Genz 644282™ ([8,9-dimethoxy-5-(2-N-methylaminoethyl)-2,3-methylenedioxy-5H-dibenzo[c,h][1,6]naphthyridin-6-one]) by the HFt-Glu-MP-PASE (containing 4 non-native glutamates per monomer, 96 per 24-mer). The relative yields are indicated in terms of % protein recovery and number of drug molecules conjugated.

FIG. 14 shows the in vitro killing efficacy of free Genz 644282™ ([8,9-dimethoxy-5-(2-N-methylaminoethyl)-2,3-methylenedioxy-5H-dibenzo[c,h][1,6]naphthyridin-6-one]) and HFt-Glu-MP-PASE-Genz against human cell lines of different origin. Values represent the mean±SEM (n=3).

DETAILED DESCRIPTION OF THE INVENTION

Figure 1:
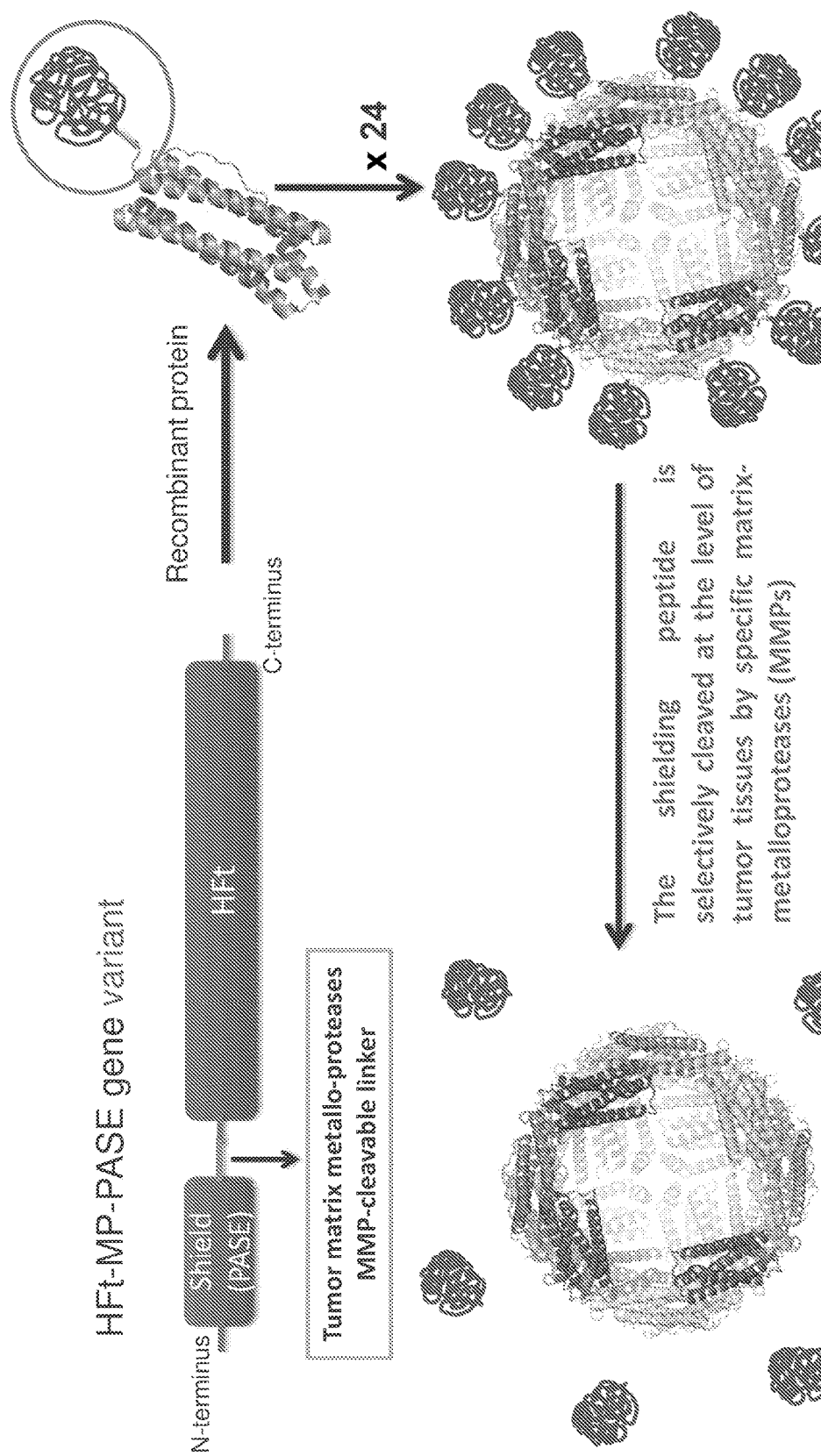
FIG. 1 is a schematic representation of the manufacture of HFt-based nanoparticles, wherein the N terminus of each of the 24 monomers is genetically bound to cleavable peptide sequences and to sequences essentially consisting of proline, alanine, serine and glutamate (PASE).

The fusion protein which is the subject matter of the present invention comprises at least three domains.

The first domain comprises the amino acid sequence of the heavy chain of the human ferritin. Such an amino acid sequence is the native sequence having at least 90% sequence identity. Since the heavy chain of human ferritin has a length of 183 amino acids (SEQ ID NO: 1), a variant having at least 90% sequence identity contains up to 19 amino acid substitutions compared to the native sequence.

In one embodiment the heavy chain of human ferritin is a mutein wherein the cysteine residues from the protein surface are removed and at least one cysteine or negative (aspartate or glutamate) residue is inserted in the internal cavity of the protein, preferably two, three or four cysteine or aspartate or glutamate are inserted in the internal cavity of the protein. The native cysteine residues from the protein surface are replaced with a residue without a thiol reactive group, preferably the cysteine will be replaced with a serine. The protein surface of the of human ferritin is herein defined as any residues exposed to the solvent. The internal cavity of the of human ferritin is herein defined as any residues not exposed to the solvent.

For example, in one embodiment the cysteine is inserted instead of the Lysine 71, of Lysine 143 and/or of Glycine 182.

In one preferred embodiment the heavy chain of human ferritin is the amino acid sequence SEQ ID NO: 2 of the HFt variant (HFt-Cys1) lacking the native cysteine residues and containing three non-native cysteine residues in the internal cavity, which represent an alternative variant. The amino acid sequence of HFt-Cys1 is characterized by six amino acid substitutions: Serine instead of Cysteine 90, Serine instead of Cysteine 102, Serine instead of Cysteine 130, Cysteine instead of Lysine 71, Cysteine instead of Lysine 143 and Cysteine instead of Glycine 182.

In one preferred embodiment the heavy chain of human ferritin lacks the native cysteine residues and containing four non-native cysteine residues in the internal cavity, which represent an alternative variant (HFt-Cys2). The amino acid sequence of this further variant is characterized by seven amino acid substitutions: Serine instead of Cysteine 90, Serine instead of Cysteine 102, Serine instead of Cysteine 130, Cysteine instead of Lysine 53, Cysteine instead of Lysine 71, Cysteine instead of Threonine 135 and Cysteine instead of Lysine 143.

In one preferred embodiment the heavy chain of human ferritin lacks the native cysteine residues and containing four non-native glutamates residues in the internal cavity, which represent an alternative variant (HFt-Glu). The amino acid sequence of this further variant is characterized by seven amino acid substitutions: Serine instead of Cysteine 90, Serine instead of Cysteine 102, Serine instead of Cysteine 130, Glutamate instead of Lysine 53, Glutamate instead of Lysine 71, Glutamate instead of Threonine 135 and Glutamate instead of Lysine 143.

All the muteins/variants of the of human ferritin herein disclosed are objects of the invention. All the herein disclosed embodiments of the heavy chain of human ferritin may be used as first domain in the fusion protein according to the invention.

The aminoacid sequence of the native HFt is (considering that the first Methionine is the start of the coding region and could be removed in later processing of the protein):

(SEQ ID NO 1)
MTTASTSQVRQNYHQDSEAAINRQINLELYASYVYLSMSYYFDRDDVAL

K-NFAKYFLHQSHEEREHAEKLMKLQNQRGGRIFLQDIKKPDCDDWESG

LNAME-CALHLEKNVNQSLLELHKLATDKNDPHLCDFIETHYLNEQV-K

AIKELGDHVTNLRKMGAPESGLAEYLFDKHTLGDSDNES

In some embodiments, the fusion protein HFt of the invention comprises a HFt variant (HFt Cys1) lacking the native cysteine residues on the external surface and containing three non native cysteines residues in the internal cavity. In one embodiment, the amino acid sequence of the variant HFt Cys1 is:

(SEQ ID NO 2)
MTTASTSQVRQNYHQDSEAAINRQINLELYASYVYLSMSYYFDRDDVAL
K-NFAKYFLHQSHEEREHAEKLMCLQNQRGGRIFLQDIK-KPDSDDWES
GLNAMESALHLEKNVNQSLLELHKLATDKNDPHLSDFIETHYL-NEQVC
AIKELGDHVTNLRKMGAPESGLAEYLFDKHTLGDSDNEC

The amino acid sequence of the variant HFt Cys2 is:

(SEQ ID NO 15)
MTTASTSQVRQNYHQDSEAAINRQINLELYASYVYLSMSYYFDRDDVAL
K-NFACYFLHQSHEEREHAEKLMCLQNQRGGRIFLQDIK-KPDSDDWES
GLNAMESALHLEKNVNQSLLELHKLATDKNDPHLSD-FIECHYLNEQVC
AIKELGDHVTNLRKMGAPESGLAEYLFDKHTLGDSDNES

In some embodiments, the fusion protein HFt of the invention comprises a HFt variant (HFt Glu) lacking the native cysteine residues on the external surface and containing four non native glutamates residues in the internal cavity. In one embodiment, the amino acid sequence of the variant HFt Glu is:

(SEQ ID NO: 18)
MTTASTSQVRQNYHQDSEAAINRQINLELYASYVYLSMSYYFDRDDVAL
K-NFAEYFLHQSHEEREHAEKLMELQNQRGGRIFLQDIK-KPDSDDWES
GLNAMESALHLEKNVNQSLLELHKLATDKNDPHLSDFIEE-HYLNEQVE
AIKELGDHVTNLRKMGAPESGLAEYLFDKHTLGDSDNES

The second domain of the fusion protein of the invention comprises the amino acid sequence of at least one matrix metalloproteinase (MMP) cleavage site, particularly MMP 2, MMP 3, MMP 7 or MMP 9. As a non limiting example, hereinafter a few peptides are listed, which simulate the cleavage sequence of the collagen chain and are cleaved in a particularly effective way by MMP 2 and MMP 9:

(SEQ ID NO: 3)
Gly Pro Leu Gly Ile Ala Gly Gln (SEQ ID NO: 4)
Gly Pro Gln Gly Ile Trp Gly Gln (SEQ ID NO: 5)
Pro Leu Gly Leu Ala Gly (SEQ ID NO: 6)
Pro Val Gly Leu Ile Gly (SEQ ID NO: 7)
Cys Gly Leu Asp Asp

The amino acid sequences that contain the cleavage site for the intended enzyme can also be constructed in such a way that the cleavage site is repeated several times, such as for instance in the sequence as shown below:

(SEQ ID NO: 8)
Gly Pro Leu Gly Ile Ala Gly Gln Gly Pro Leu Gly Ile Ala Gly Gln.

All the previously mentioned amino acid sequences are representative, but not limitative, examples of the manufacture of the fusion proteins and the nanoparticles according to the present invention.

The third domain of the fusion protein of the invention, linked to the N terminus, essentially consists or consists of the amino acid sequence of a polypeptide which is rich in proline, serine, alanine and at least one negative amino acids such as glutamate or aspartate (referred to as "PASE" for the sake of brevity), having the aim of increasing the stability of the protein during the drug encapsulating process, especially with drugs that can promote protein protein aggregation, and of increasing the stability of the protein drug complex in comparison to the polypeptide lacking the negative amino acids (PAS).

The polypeptide PASE essentially consists of amino acid sequences rich in Pro, Ala and Ser, and at least one or more Glu and/or Asp which form a negatively charged unstructured polymer, the length of which is preferably lower than 80 amino acid residues, more preferably comprised between 20 and 80 amino acid residues, still more preferably comprised between 30 and 70 amino acid residues. In a preferred embodiment, the proline residues of the aforesaid polypeptide PASE amount to 10 40% of the total amino acid residues of the polypeptide PASE.

According to one embodiment the PASE domain will comprise one, two, three or four glutamate and/or aspartate. In one preferred embodiment the PASE domain comprises no more than one glutamate or aspartate within 15, 16, 17, 18, 19 or 20 residues of the PAS domain.

Examples of PASE polypeptides particularly suitable to be used within the scope of the present invention, and therefore preferred, are the following:

(SEQ ID NO: 9)
ASPAAPAPASPAAPAPSAPAEASPAAPAPASPAAPAPSAPAE;

(SEQ ID NO: 10)
ASPAAPAPASPAEPAPSAPAASPAAPAPASPAEPAPSAPA;

(SEQ ID NO: 11)
ASPAAPAPASPAAPAPSAPAEASPAAPAPASPAAPAPSAPAEASPAAPAP
AS-PAAPAPSAPAEASPAAPAPAS;

(SEQ ID NO: 12)
ASPAAPAPASPAAPAPSAPADASPAAPAPASPAAPAPSAPAD;

(SEQ ID NO: 13)
ASPAAPAPASPADPAPSAPAASPAAPAPASPADPAPSAPA;

(SEQ ID NO: 14)
ASPAAPAPASPAAPAPSAPADASPAAPAPASPAAPAPSAPADASPAAPAP
AS-PAAPAPSAPADASPAAPAPAS;

All the PASE domains herein disclosed are objects of the present invention.

With the term "the polypeptide essentially consists of amino acid sequences rich in Pro, Ala and Ser" in the present description is defined a polypeptide that form a stable random coil conformation that consists of Pro, Ala and Ser wherein from 1 to 5% of Pro, Ala and Ser residues are replaced with other amino acid, such for example glycine, that do not alter the stable random coil conformation of the polypeptide. As mentioned above, the biosynthetic random coil polypeptides (or random coil polypeptide segments) of this invention consisting solely of proline and alanine residues and at least one residue of glutamate or aspartate and form a stable random coil conformation. The term "random coil" as used herein relates generally to any conformation of a polymeric molecule, including amino acid polymers/amino acid sequences/polypeptides, in which the individual monomeric elements that form said polymeric structure are essentially randomly oriented towards the adjacent monomeric elements while still being chemically bound to said adjacent monomeric elements. In particular, a polypeptide, amino acid sequence or amino acid polymer adopting/having/forming "random coil conformation" substantially lacks a defined secondary and tertiary structure. The nature of polypeptide random coils and their methods of experimental identification are known to the person skilled in the art and have been described in the scientific literature (Cantor (1980) Biophysical Chemistry, 2nd ed., W.H. Freeman and Company, New York; Creighton (1993) Proteins—Structures and Molecular Properties, 2nd ed., W.H. Freeman and Company, New York; Smith (1996) Fold Des 1:R95 R106).

The stabilizing and masking PASE polypeptide is added to the surface of HFt through a short peptide sequence that, as previously mentioned above, contains one or more metallo proteinase cleavage sites, so as to provide the fusion protein of the invention with a displaceable masking. In fact, PASE polypeptide can be selectively removed at the target tissues by extracellular matrix metalloproteinases (MMPs). MMP 2 and MMP 9 were shown to be key metalloproteinases that are overexpressed in the tumor microenvironment and are involved in angiogenesis, invasion, and tumor metastasis.

It's also a further object of the invention a fusion protein wherein the PASE or PAS domain and the MMP cleavable domains are linked the C terminus of the HFt protein instead of the N terminus. According to one embodiment the fusion protein has the SEQ ID NO:16 or SEQ ID NO:17.

PAS MP HFt
(SEQ ID NO: 16)
MTTASTSQVRQNYHQDSEAAINRQINLELYASYVYLSMSYYFDRDDVAL

K-NFAKYFLHQSHEEREHAEKLMKLQNQRGGRIFLQDIKKPDCDDWESG

LNAME-CALHLEKNVNQSLLELHKLATDKNDPHLCDFIETHYLNEQV-K

AIKELGDHVTNLRKMGAPESGLAEYLFDKHTLGDSDNESPLGLAGASPA

APA-PASPAAPAPSAPAASPAAPAPASPAAPAPSAPA

PASE MP HFt
(SEQ ID NO: 17)
MTTASTSQVRQNYHQDSEAAINRQINLELYASYVYLSMSYYFDRDDVAL

K-NFAKYFLHQSHEEREHAEKLMKLQNQRGGRIFLQDIKKPDCDDWESG

LNAME-CALHLEKNVNQSLLELHKLATDKNDPHLCDFIETHYLNEQV-K

AIKELGDHVTNLRKMGAPESGLAEYLFDKHTLGDSDNESPLGLAGASPA

APA-PASPAEPAPSAPAASPAAPAPASPAEPAPSAPA

The use of PASE polypeptides on the multimeric surface of ferritin within the scope of the present invention offers several advantages over the prior art. To obtain higher yields and monodispersed materials during the protein drug complex formation, we genetically reengineered previous reported HFt MP PAS by adding glutamate (E) or aspartate (D) residues in the PAS sequence and obtained a new construct, named HFt MP PASE. Thanks to this modification, ferritin based proteins could form complexes with drugs that can promote protein aggregation (e.g. mitoxantrone and pixantrone) in a manner more soluble and monodispersed than the native HFt or the modified HFt MP PAS counterpart.

This improvement of the stability of the protein drug complex encapsulation yields different from doxorubicin (e.g. mitoxantrone and pixantrone), have been surprisingly and unexpectedly achieved by the present inventor, who constructed nanoparticles based on the heavy chain of human ferritin (HFt), by using both the gene fusion technology and the production technology of recombinant proteins. In particular, as will be described in detail in the section related to the examples, genetic constructs were made, which, in one single nucleic acid sequence (for instance DNA), encode for the three sequences set forth in FIG. 1: i) HFt; ii) short peptide sequences (MP) cleavable by MMP 2/9; iii) unstructured polypeptide sequences rich in Pro, Ser, Ala and Glu (PASE) preferably with a length comprised between 20 and 80 residues. Sequences ii) and iii) are bound to the N terminus of HFt for a reversible masking thereof.

Figure 2:
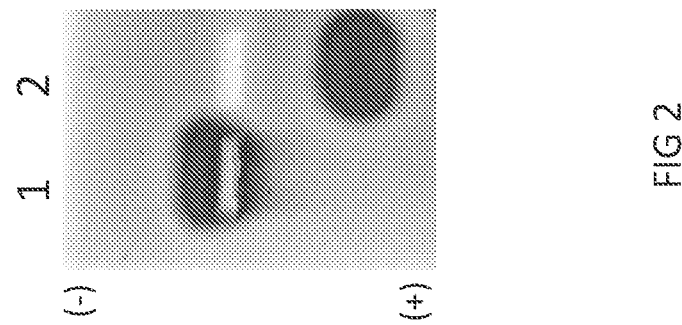
FIG. 2 shows native agarose gel electrophoresis band migration profiles. Lane HFt-MP-PAS (15 μg); Lane 2, HFt-MP-PASE (15 μg).

As already stated above, the HFt fusion proteins obtained by the present inventors spontaneously form HFt nanoparticles capable of carrying therapeutic (chemical compounds, monoclonal antibodies, peptides, etc.) (FIG. 2).

In one embodiment one or more, preferably 5, therapeutic and/or diagnostic molecules are encapsulated in the inner cavity of the HFt nanoparticle or are covalently bound to the surface of the HFt nanoparticle or are covalently bound in the inner cavity of the HFt. The amount of bound drug and the homogeneity of the protein drug complex itself are considerably increased compared to the unmodified protein (HFt) or to the PAS modified one (HFt MP PAS) thanks to the presence of the PASE polypeptides. The homogeneity of the material obtained is a highly desirable property in the pharmaceutical field, as it indicates the absence of negative effects, such as precipitation, clustering, and loss of the final product carrying the therapeutic molecule.

A therapeutic molecule is for example a pharmaceutical active ingredient. As used herein, the expression "pharmaceutical active ingredient" or more simply "active ingredient" refers to any pharmaceutically active molecule (chemical compound, monoclonal antibody, peptide, etc.), for instance a molecule that can be used for cancer treatment. Preferred active ingredients for use in the present invention are for example, without limitation, doxorubicin, mitoxantrone, pixantrone, Genz 644282™ ([8,9-dimethoxy-5-(2-N-methyl aminoethyl)-2,3-methylenedioxy-5H-dibenzo[c,h][1,6]naphthyridin-6-one]), paclitaxel, auristatins, camptothecins, gemcitabine and platinum based active ingredients. A precursor of the active ingredients listed above may also be used.

In therapeutic applications, the HFt nanoparticles of the present invention, which act as targeted carrier systems, can be administered to a subject or patient through any suitable administration route, for instance orally, parenterally, intravenously, intraperitoneally, intramuscularly, as a suppository, intralesionally, intranasally or subcutaneously, intrathecally, intralymphatically, through inhalation of microdroplets, or by implant of a slow release device, for instance an osmotic pump. As used herein, the term "subject" relates to animals, such as mammals, including human beings, cows, sheep, goats, horses, dogs, cats, rabbits, rats, mice and the like.

As used herein, the term "treating" or "treatment" refers to evidence of success or improvement in the treatment of a certain disease, lesion, condition or symptom, or, in certain circumstances, the prevention of the onset of a symptom or condition.

In therapeutic applications, the HFt nanoparticles of the invention are used for the administration of a therapeutically effective dose of a pharmaceutical active ingredient. "Therapeutically effective dose" is intended to mean a dose that produces the therapeutic effect for which it is administered.

The exact dose will depend on a number of factors, including the aim of the treatment, the subject, the disease to be treated, etc., and can easily be determined by a person of ordinary skill in the art by using per se known methodologies (see, for example, Lieberman, Pharmaceutical Dosage Forms (vols. 1 3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

The HFt nanoparticles of the invention may be used for treating any disease that requires the administration of a pharmaceutical ingredient, for instance by sequestering the active ingredient within the cavity of the nanoparticle or by covalently binding it to the nanoparticle surface. The nanoparticles can also be used for diagnosis, more particularly for the imaging of diseases, by sequestering an imaging agent within the cavity of the nanoparticle or by covalently binding it to the nanoparticle surface.

The HFt nanoparticle of the present invention can be administered to a subject for the treatment of any disease, preferably a hyperproliferative disease, including cancer, for example: carcinomas, gliomas, mesotheliomas, melanomas, sarcomas, lymphomas, leukaemias, adenocarcinomas, breast cancer, ovary cancer, cervical cancer, glioblastoma, leukaemia, lymphoma, prostate cancer, Burkitt's lymphoma, head and neck cancer, colon cancer, colorectal cancer, non small cell lung cancer, small cell lung cancer, oesophagus cancer, stomach cancer, pancreatic cancer, hepatobiliary cancer, bladder cancer, small intestine cancer, rectal cancer, kidney cancer, gall bladder cancer, penile cancer, urethra cancer, testicular cancer, cervix cancer, vaginal cancer, uterine cancer, thyroid cancer, parathyroid cancer, adrenal cancer, endocrine pancreatic cancer, carcinoid tumor, bone cancer, skin cancer, retinoblastomas, multiple mielomas, Hodgkin lymphoma, non Hodgkin lymphoma (see CANCER: PRINCIPLES AND PRACTICE (DeVita, V. T. et al. 2008 Edition) for other types of cancer).

According to one embodiment the HFt nanoparticle are bound to every molecule containing a thiol reactive motif, e.g. drugs, linkers, fluorophores, etc. using for example one or more cysteines inserted in the internal cavity. According to one preferred embodiment the HFt nanoparticle encapsulates a 6 maleimidocaproyl hydrazone derivative of Doxorubicin (DOX EMCH) or the linker maleimido propionic acid and the drug Genz 644282™ ([8,9-dimethoxy-5-(2-N-methylaminoethyl)-2,3-methylenedioxy-5H-dibenzo[c,h][1,6]naphthyridin-6-one]) using one or more cysteines inserted in the internal cavity.

The following examples are provided for illustrative purposes and not as a limitation of the scope of the invention as defined in the appended claims.

EXAMPLES

Example 1

Construction of Expression Vectors for HFt-MP-PASE Fusion Proteins

As an attempt to reduce protein aggregation and increase stability, it was decided to introduce negatively charged residues in the outer shield forming PAS sequence fused to each HFt subunit. Indeed, analysis of the previously obtained HFt-MP-PAS construct suggested that introduction of two glutamate residues in a PAS sequence of 40 residues would cause sufficient electrostatic repulsion to prevent aggregation between different 24 meric assemblies, without affecting subunit assembly within the 24 mer. To distribute the negative charges on the surface of the construct as much as possible, glutamic acid residues were placed at a distance of 20 residues.

The HFt-MP-PASE gene was achieved by combining three different sequences into one single sequence: HFt (SEQ ID NO: 1), MP (SEQ ID NO: 5) and PASE (SEQ ID NO: 10). This construct differs from the previously disclosed HFt-MP-PAS construct (named previously HFt MMP PAS40; WO2016051340) only for two aminoacid substitutions in the PAS sequence: Glutamate instead of Alanine 13 and Glutamate instead of Alanine 33. Every comparative experiments disclosed in this novel patent was performed using these two constructs.

The pET 11a expression vector containing the HFt-MP-PASE gene was synthesized by using GENEART AG (Germania). Gene synthesis was carried out taking into consideration the codon optimization for high levels of expression in *Escherichia coli*.

The fusion protein HFt MP PASE was obtained via recombinant protein technology and purified from the cellular soluble fraction at high yield, similar to HFt-MP-PAS (about 150 mg per liter of *E. coli* cell culture). The effect on protein mobility of the negatively charged glutamate residues (48 per protein) inserted on the protein surface was assessed by performing agarose gel electrophoresis under native conditions (FIG. 1). At variance with denaturant SDS PAGE, in native electrophoresis protein mobility depends on both protein charge and molecular mass. Assuming the latter to be comparable for HFt MP PAS and HFt MP PASE, the observed difference in protein mobility has to be ascribed to the additional negative charges in the HFt-MP-PASE construct (FIG. 2).

Example 2

Preparation of HFt-MP-PAS and HFt-MP-PASE Carrying Chemotherapeutic Drugs

Figure 3:
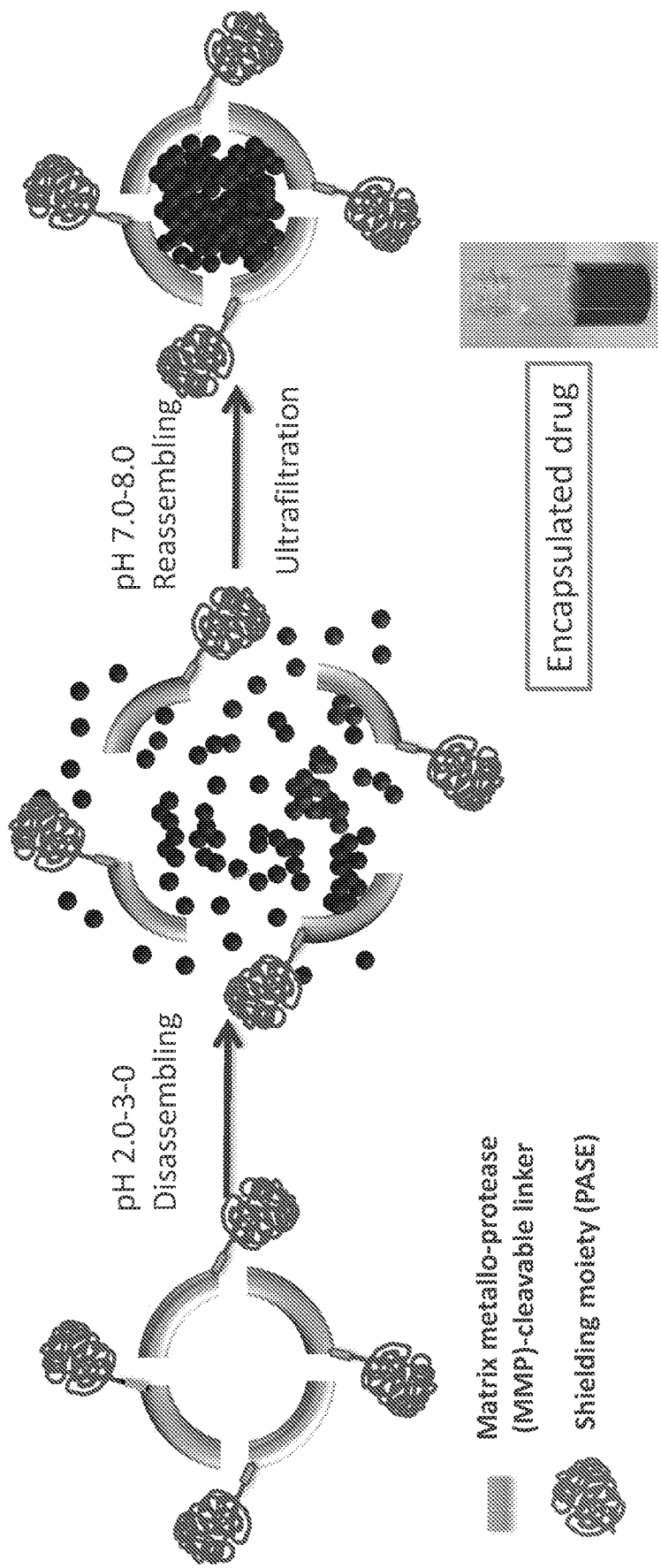
FIG. 3 is a schematic representation of the synthesis of HFt-MP-PASE containing the drug mitoxantrone (MIT) or pixantrone (PIX). For clarity purposes, only 4 out of the 24 modified HFt N-termini are shown.

As chemotherapeutic agents, the inventor reported an example in which the drugs mitoxantrone (MIT) or pixantrone (PIX) were used. These drugs were encapsulated within the protein cavity of the fusion proteins by exploiting the protein uncoupling coupling process as a function of the pH according to protocol disclosed in Falvo et al., 2016, Biomacromolecules. 17(2):514 22. The disassembly/reassembly procedure is shown in FIG. 3.

Example 3

Testing of the Encapsulating Yields of the Drug Mitoxantrone and Pixantrone

The efficiency of MIT or PIX encapsulation in HFt-MP-PASE was compared to that of the native HFt and in the HFt MP PAS (FIG. 4). In all experiments performed, HFt-MP-PASE outperforms both the native HFt and the HFt-MP-PAS proteins in terms of the amount of protein recovered at the end of the reactions. This indicate that HFt-MP-PASE is more stable and does not aggregate/precipitate out of the solution during the protein drug complex formation.

Example 4

Testing of the Homogeneity and Stability of the Protein Mitoxantrone Complex

Figure 5:
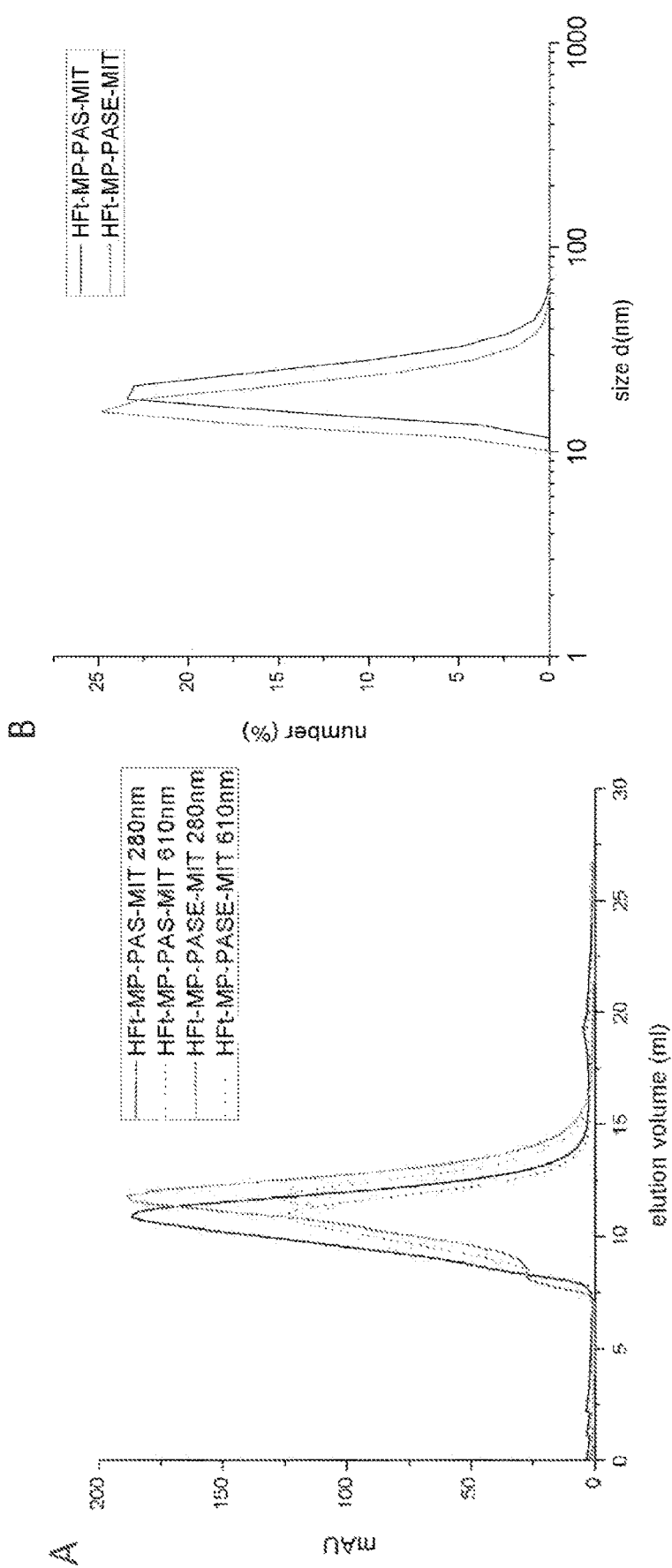
FIG. 5 shows the gel-filtration elution profiles (SEC) and particle size distribution (DLS) of HFt-based constructs. (A) SEC analysis of MIT-loaded HFt-MP-PAS (black) and HFt-MP-PASE (red) constructs. Elution profiles obtained following simultaneously protein and MIT contributions at 280 nm (solid) and 610 nm (dotted), respectively. (B) DLS profiles of the same constructs.

MIT loaded HFt-MP-PASE complex were more soluble and monodispersed than the HFt-MP-PAS counterparts, displaying no higher molecular weight species in solution (FIG. 5). Dynamic light scattering (DLS) experiments indicated that HFt-MP-PASE-MIT samples have approximately the same size as our previously reported HFt-MP-PAS-DOX (containing doxorubicin as drug), with a mean diameter of 17.0±1.1 nm (FIG. 5B). These results indicate that insertion of the glutamate residues in HFt-MP-PASE-MIT surprisingly leads to much higher protein solubility and homogeneity compared to the HFt-MP-PAS counterpart, likely preventing MIT mediated protein protein interactions in solution. In addition, the slightly higher number of MIT molecules per 24 mer observed for HFt-MP-PAS in comparison to HFt-MP-PASE (55.0 vs 49.0) can be likely ascribed to the presence of MIT molecules on the surface of the former construct that may promote protein protein aggregation.

Figure 6:
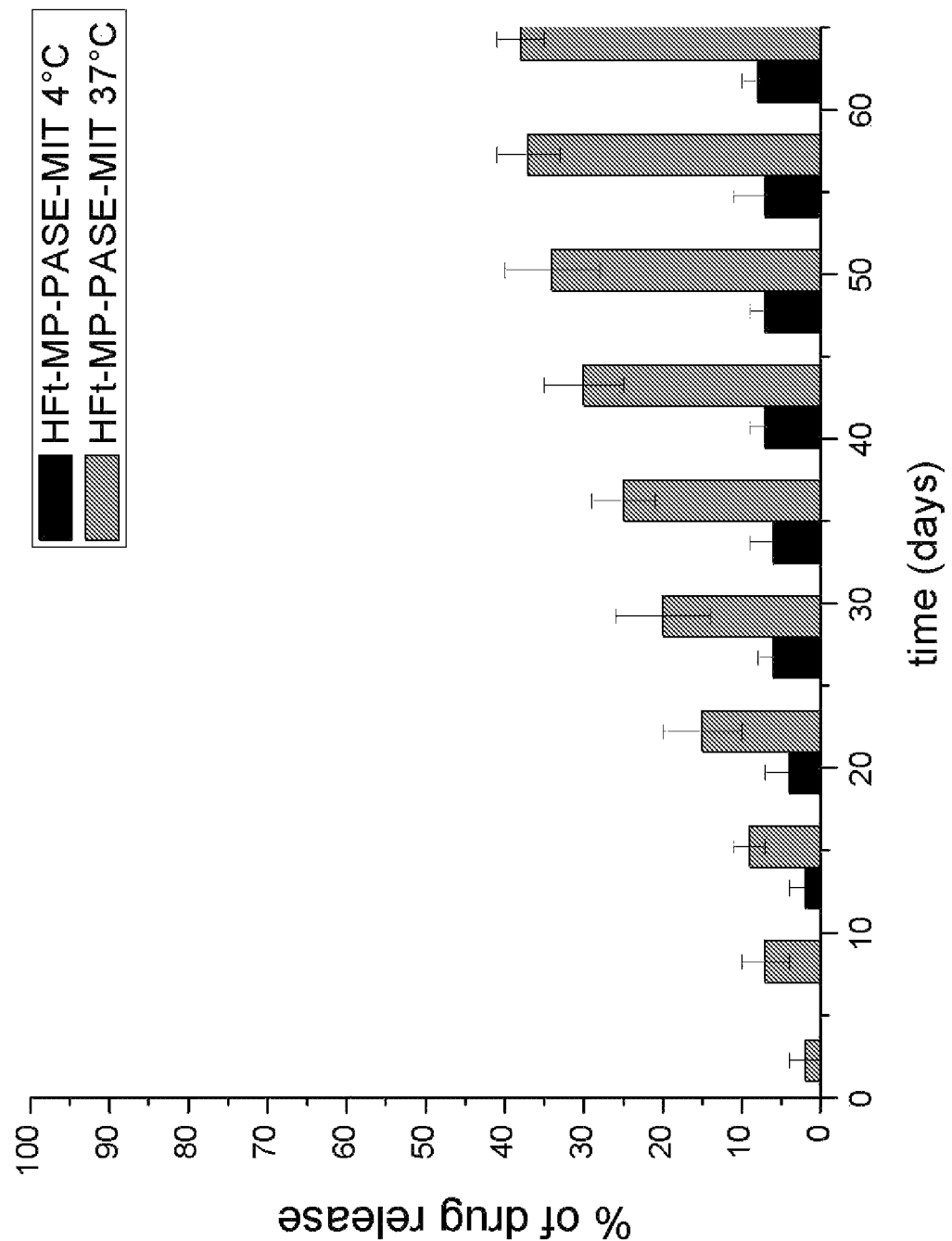
FIG. 6 shows the drug release from HFt-MP-PASE-MIT complexes. MIT-loaded nanocarriers were stored at 4° C. and 37° C. in PBS and assayed for their mitoxantrone content by SEC at given times. The percentage of mitoxantrone leakage was assessed by comparing the elution profiles simultaneously collected at 280 nm and 610 nm.

The stability of the HFt-MP-PASE-MIT complexes was tested by storing the solutions for 2 months in PBS at 4° C. or 37° C. and evaluating their MIT content by size chromatography (SEC) analysis every 7 days. HFt-MP-PASE-MIT showed excellent stability, with less than 10% MIT being released after 2 months storage at 4° C. (FIG. 6) and no sign of turbidity or precipitation.

Example 5

Testing of the Cell Internalization and Localization of HFt Based Nanocarriers

Figure 7:
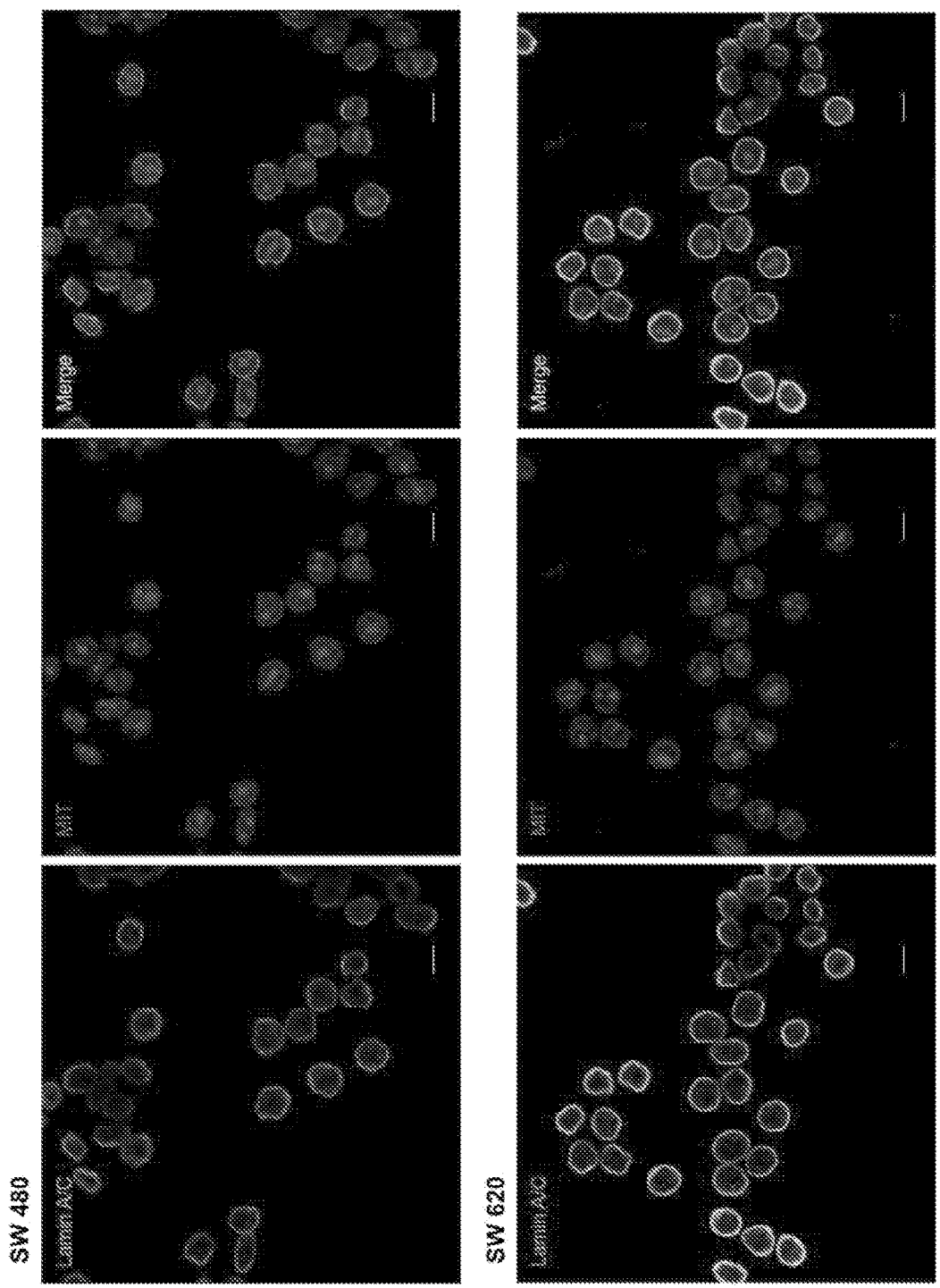
FIG. 7 shows the HFt-MP-PASE-MIT (20 μM MIT concentration) localization in SW480 (upper panel) and SW620 (lower panel) colon cancer cell lines after 3 h-incubation. Left panels: Lamin A/C staining (nuclear membrane marker, green); central panels: MIT (blue); right panels: merge. The white bar indicates a 10 μm length.

To determine whether MIT containing HFt based constructs undergo cell surface binding and/or internalization, they were incubated with colon cancer cells SW480 and SW620 at 37° C. for 1 or 3 h and MIT associated fluorescence was visualized by confocal microscopy. FIG. 7 shows HFt MP PASE MIT localization in the SW480 (upper panel) and SW620 (lower panel) cell lines. After 3 hours incubations HFt-MP-PASE-MIT massively accumulate in the nuclei of both cell lines, as shown by staining with the nuclear membrane marker Lamin A/C (in green). In particular, MIT localizes in intranuclear structures assumed to be nucleoli on the basis of size, position and shape, as previously proposed for colon carcinoma and breast cancer cells.

Figure 8:
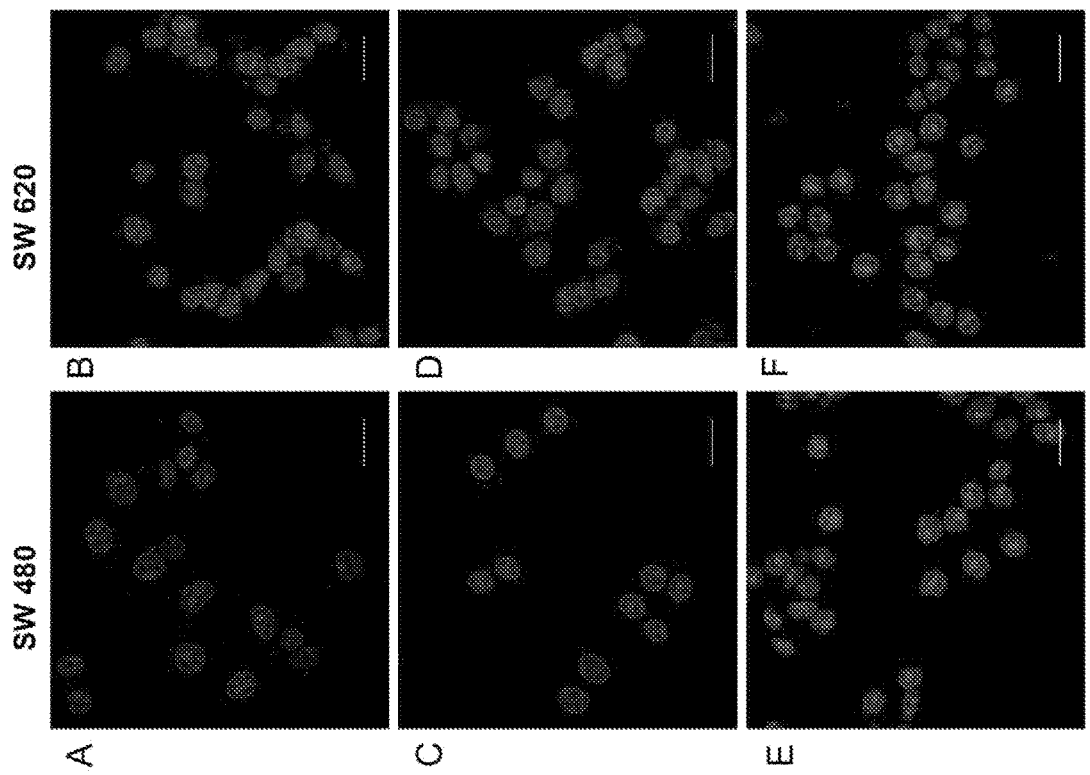
FIG. 8 shows the localization of MIT (panels A, B), HFt-MP-PAS-MIT (panels C, D) and HFt-MP-PASE-MIT (panels E, F) in SW480 (panels A, C and E) and SW620 (panels B, D and F) colon cancer cell lines after 3 h incubation. MIT concentration is 20 μM in all experiments. The white bar indicates a 20 μm length.

A comparison between cells treated with free MIT, HFt-MP-PAS-MIT or HFt-MP-PASE MIT is shown in FIG. 8. In all cases MIT localizes inside the cell nuclei, but in the case of free MIT and HFt-MP-PAS-MIT the drug is partly present also in the cytoplasm. Overall, cells treated with HFt-MP-PASE-MIT showed the highest accumulation of MIT in the nuclei.

Example 6

Anti Proliferative Effects of HFt MP PASE MIT In Vitro

To assess the ability of MIT loaded HFt-MP-PASE to kill cancer cells in vitro, we have performed XTT viability assays on a wide range of human cancer cells of different origin: fibrosarcoma HT1080; triple negative breast MDA MB 231; pancreatic PaCa 44, Capan 1 and MiaPaCa2; colorectal SW480 and SW620 cancer cells.

Not only MIT preserved its pharmacological activity after encapsulation in HFt MP PASE constructs, but the MIT loaded nanocarrier display IC50 values similar to those of naked MIT in all cell lines tested, and even lower in some cases (see FIG. 9). This is remarkable in that naked drugs can freely diffuse into cells, whereas the HFt-MP-PASE constructs can only deliver MIT by undergoing rate limiting receptor mediated uptake. Moreover, the new nanosystem HFt-MP-PASE-MIT showed, on the pancreatic cell lines, a killing efficacy of about ten time higher than the currently used drug Gemcitabine (i.e. 0.43 vs 6.75 µM, 0.10 vs 2.8 µM and 0.07 vs 1.15 for Paca44, Capan 1 and MiaPaCa2 cells respectively).

Example 7

Biodistribution Experiments on Doxorubicin Containing Compounds in Mice

Figure 10:
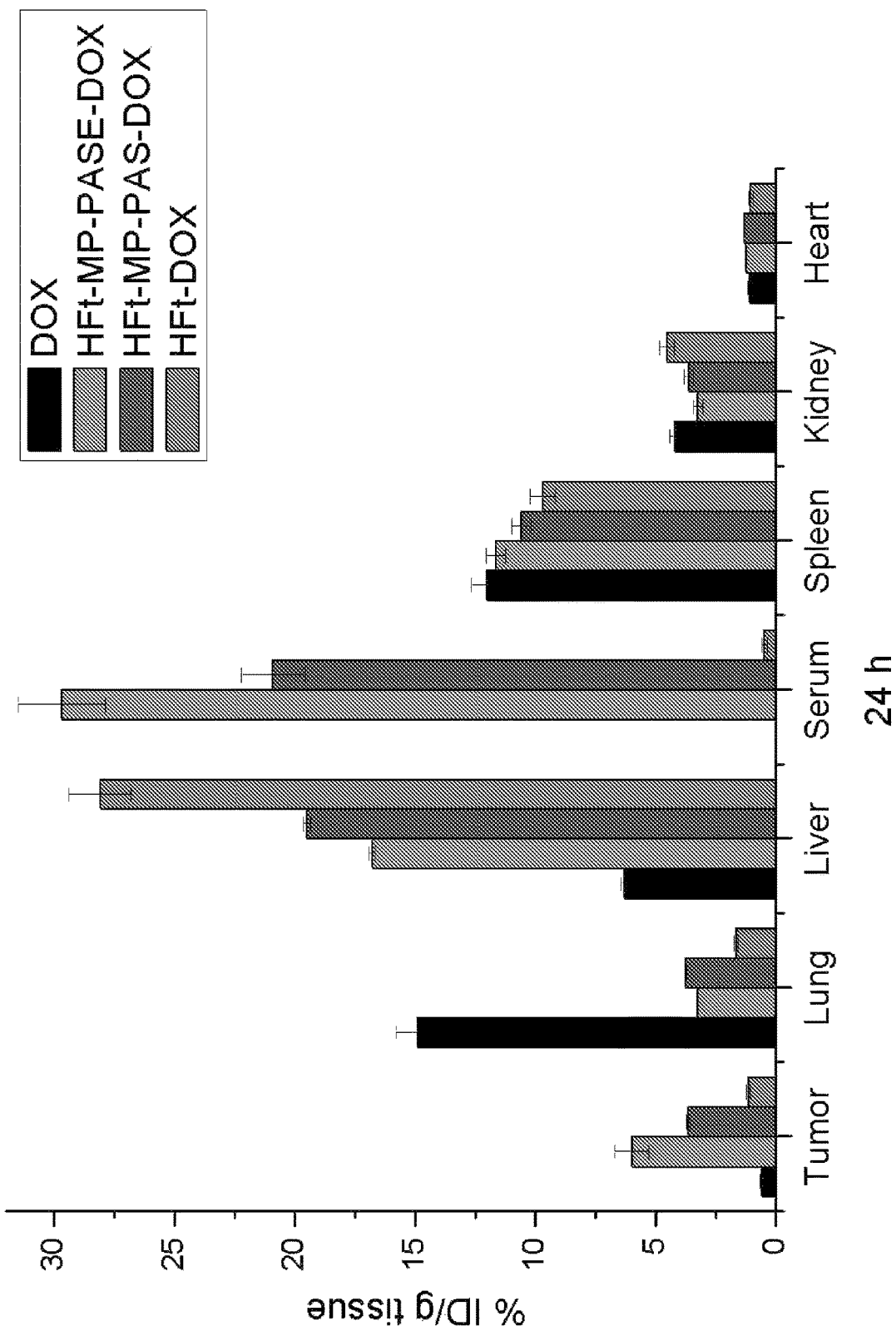
FIG. 10 shows the results from biodistribution experiments on doxorubicin-containing compounds. Doxorubicin plasma concentrations were calculated at 24 hour after intravenous injections in mice bearing a human pancreatic tumor (Xenografts) of the naked drug doxorubicin, or of doxorubicin encapsulated in the ferritin-based compounds: native HFt, HFt-MP-PAS and HFt-MP-PASE.

To compare how HFt-MP-PASE compares with HFt-MP-PAS in terms of tumor and organs drug accumulation, both fusion proteins were encapsulated with a drug. As drug was chosen Doxorubicin (DOX) as both fusion proteins have similar ability in encapsulating it, in contrast to the mitoxantrone drug. Dox plasma concentrations were calculated at 24 hours after intravenous injections in mice bearing a human pancreatic tumor (Xenografts) of the naked drug Dox, or of doxorubicin encapsulated in the ferritin based compounds: native HFt, HFt-MP-PAS and HFt-MP-PASE. FIG. 10 shows that HFt-MP-PASE has the higher stability in serum and the higher tumor accumulation also.

Example 8

Construction of Expression Vectors for HFt-MP-PASE-Cys or Glu Fusion Proteins

Figure 11:
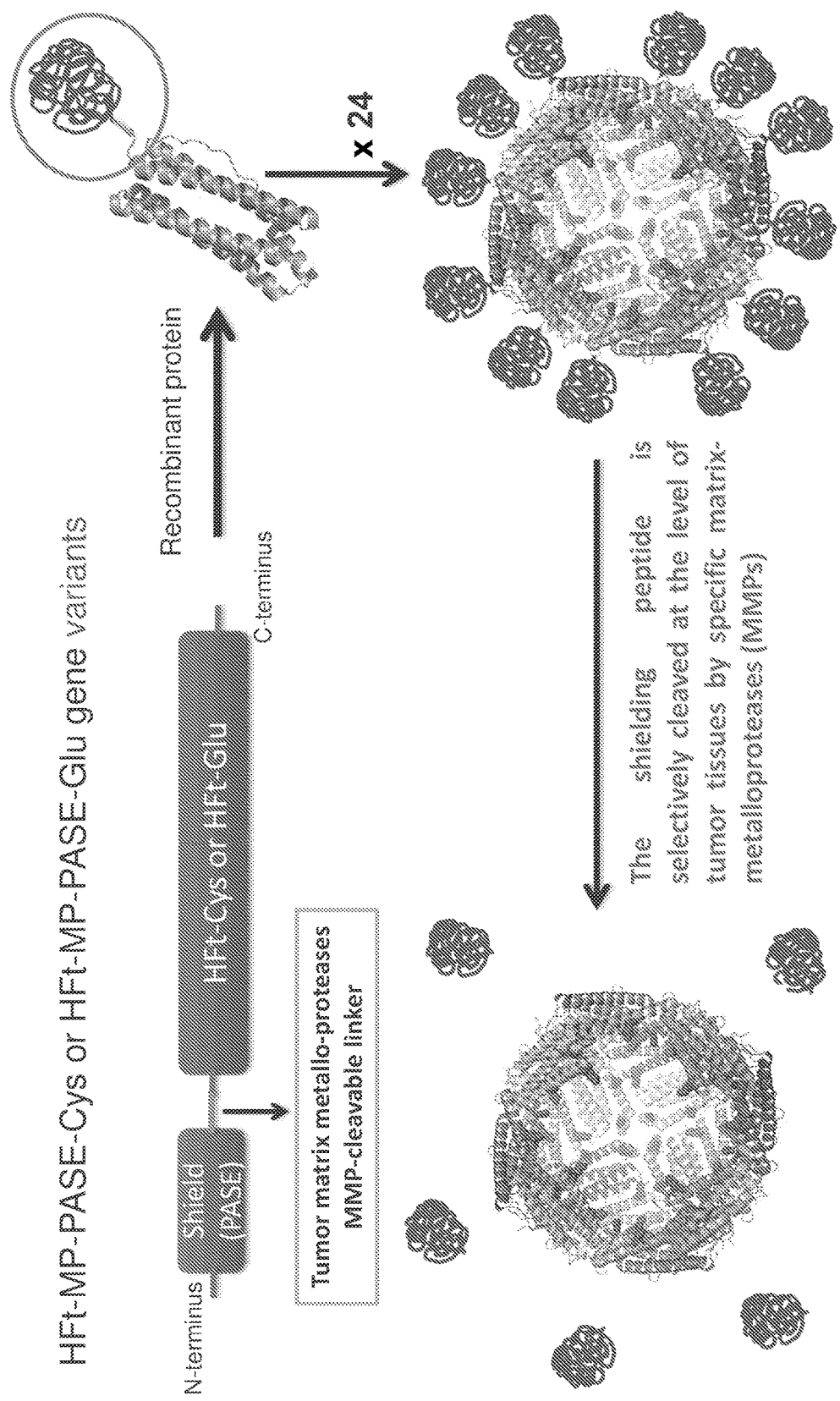
FIG. 11 is a schematic representation of the manufacture of HFt-based nanoparticles, wherein in addition to the N-terminus modifications showed previously (HFt-MP-PAS), native cysteine residues are substituted with serine residues, and non-native cysteine or glutamate residues (in red spheres) are included in the internal cavity (HFt-Cys-MP-PASE or HFt-Glu-MP-PASE).
Figure 12:
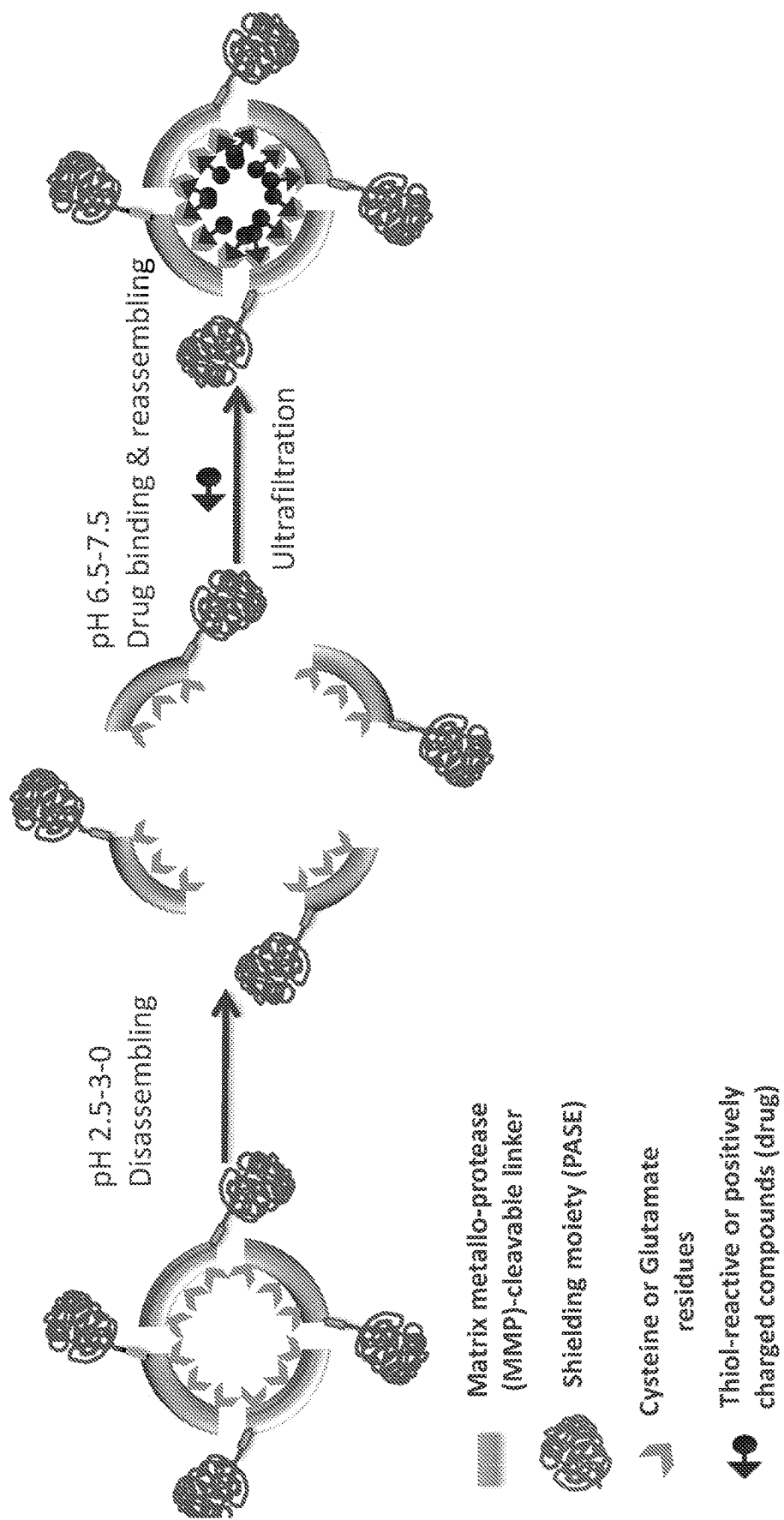
FIG. 12 is a schematic representation of the synthesis of HFt-Cys-MP-PASE or HFt-Glu-MP-PASE containing a drug reactive to thiol group of cysteines (e.g. maleimide) or a drug containing a positive motif. For clarity purposes, only 4 out of the 24 modified HFt N-termini are shown. The non-native cysteine residues in the protein internal cavity are showed in red.

As an attempt to improve and facilitate drug binding within the ferritin cavity, it was decided to remove cysteine residues from the protein surface and to introduce additional cysteine or glutamate residues in the protein cavity. In this way, it would be possible to bind to the internal cavity every molecule containing a thiol reactive or a positively charged motif, e.g drugs, linkers, fluorophores, etc. FIGS. 11 and 12 are schematic representation of the manufacture and synthesis of HFt based nanoparticles, wherein in addition to the N terminus modifications showed previously (HFt-MP-PAS), native cysteine residues are substituted with serine residues, and non native cysteine or glutamate residues (in red spheres) are included in the internal cavity (HFt-Cys-MP-PASE or HFt Glu MP PASE). FIG. 13 shows the ability to encapsulate a 6 maleimidocaproyl hydrazone derivative of Doxorubicin (DOX EMCH) by the novel HFt-Cys2-MP-PASE protein (containing 4 non native cysteines per monomer, 96 per 24 mer). In the same figure is shown also the ability of the HFt-Cys-MP-PASE to encapsulate the linker maleimido propionic acid and the drug Genz 644282™ ([8,9-dimethoxy-5-(2-N-methylaminoethyl)-2,3-methylenedioxy-5H-dibenzo[c,h][1,6]naphthyridin-6-one]). In the same figure is shown also the ability of the HFt-Glu-MP-PASE to encapsulate the free drugs mitoxantrone or Genz 644282™ ([8,9-dimethoxy-5-(2-N-methylaminoethyl)-2,3-methylenedioxy-5H-dibenzo[c,h][1,6]naphthyridin-6-one]). All these drugs were encapsulated within the protein cavity of the fusion proteins by exploiting the protein uncoupling coupling process as a function of the pH according to protocol disclosed in Falvo et al., 2016, Biomacromolecules. 17(2):514 22, with one modification. In the reactions using the maleimide containing molecules, these were added at pH 6.5 7.5 after the pH acid step to avoid possible molecule damage due to the low pH values. In addition, in the reaction using the linker maleimido propionic acid and the drug Genz 644282™ ([8,9-dimethoxy-5-(2-N-methylaminoethyl)-2,3-methylenedioxy-5H-dibenzo[c,h][1,6]naphthyridin-6-one]), the former was added before the drug at a linker/thiol ratio of 1.2:1.

The relative yields are indicated in terms of % protein recovery and number of drug molecules conjugated.

Example 9

Anti Proliferative Effects of HFt-Glu-MP-PASE Genz 644282™ ([8,9-dimethoxy-5-(2-N-methylaminoethyl)-2,3-methylenedioxy-5H-dibenzo[c,h][1,6]naphthyridin-6-one]) In Vitro

In order to test the proliferation, human sarcoma (HT 1080 and A204), human breast cancer (MDA MB 231), human melanoma (Colo38) and human pancreatic cancer (PaCa44 and MiaPaCa2) cells were plated on 96 well plates at approximately $5\times10^3$/well in 200 µl of complete medium at 37° C. The following day, the wells received Genz 644282™ ([8,9-dimethoxy-5-(2-N-methylaminoethyl)-2,3-methylenedioxy-5H-dibenzo[c,h][1,6]naphthyridin-6-one]) or HFt Glu MP PASE Genz 644282™ ([8,9-dimethoxy-5-(2-N-methyl amino ethyl)-2,3-methylenedioxy-5H-dibenzo[c,h][1,6]naphthyridin-6-one]), in triplicate, at different concentrations in Genz 644282, and the cells were cultured for 72 hours. During the last 4 hours in culture, cell viability was evaluated by the reduction of 3 (4,5 dimethylthiozol 2 yl) 2,5 diphenyltetrazolium bromide (MTT). A total of 1 mg/mL of MTT was added into each well and the samples were incubated for 30 min at 37° C. After washing, the formazan crystals were dissolved in 100 µL of dimethyl sulfoxide. The absorbance was measured at 550 nm.

The anti-proliferative effects of HFt Glu MP PASE Genz 644282™ ([8,9-dimethoxy-5-(2-N-methylaminoethyl)-2,3-methylenedioxy-5H-dibenzo[c,h][1,6]naphthyridin-6-one]) for the cultured cancer cells are shown in FIG. 14. The results indicate that HFt Glu MP PASE Genz 644282™ ([8,9-dimethoxy-5-(2-N-methylaminoethyl)-2,3-methylenedioxy-5H-dibenzo[c,h][1,6]naphthyridin-6-one]) effectively inhibits cancer cells grown in vitro in a concentration dependent way, with IC50 values identical or even lower compared to nude drug. These results are of major importance in the light of the potential therapeutic applications. The same results have been also obtained using the construct HFt-Cys-MP-PASE Genz 644282™ ([8,9-dimethoxy-5-(2-N-methylaminoethyl)-2,3-methylenedioxy-5H-dibenzo[c,h][1,6]naphthyridin-6-one]).

Anti Proliferative Effects of HFt Glu MP PASE Genz 644282™ ([8,9-dimethoxy-5-(2-n-methylaminoethyl)-2,3-methylenedioxy-5h-dibenzo[c,h][1,6]naphthyridin-6-one]) In Vivo

Figure 15:
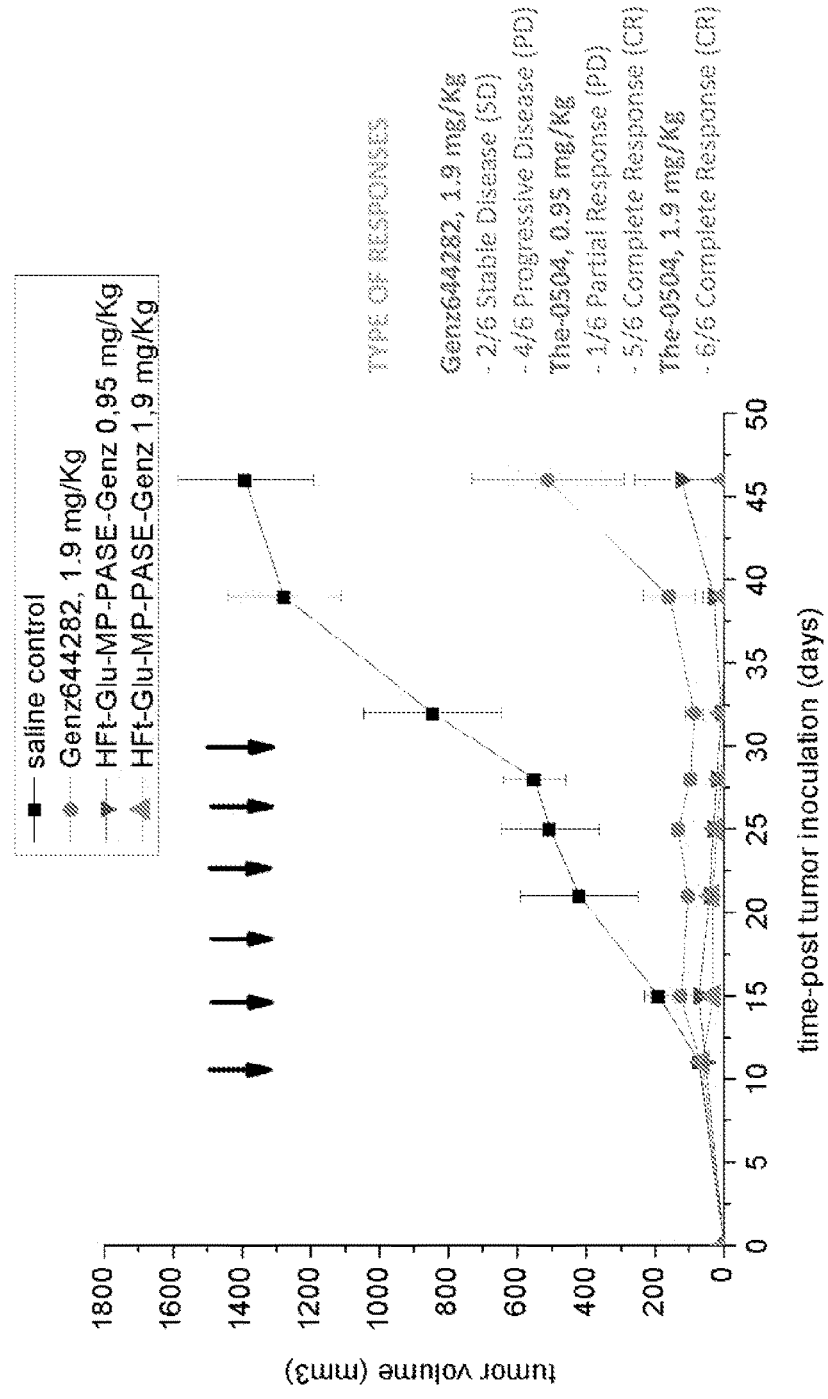
FIG. 15 shows the anti-tumor activity of free Genz 644282™ ([8,9-dimethoxy-5-(2-N-methylaminoethyl)-2,3-methylenedioxy-5H-dibenzo[c,h][1,6]naphthyridin-6-one]) and HFt-Glu-MP-PASE-Genz in pancreatic PaCa44 tumor-bearing mice. Tumor-growth curves for each mouse group are indicated. Mice were sacrificed when the tumor had reached a volume in the range 1000-1500 mm³. Arrows indicate the six days during which treatments were administered.
Figure 16:
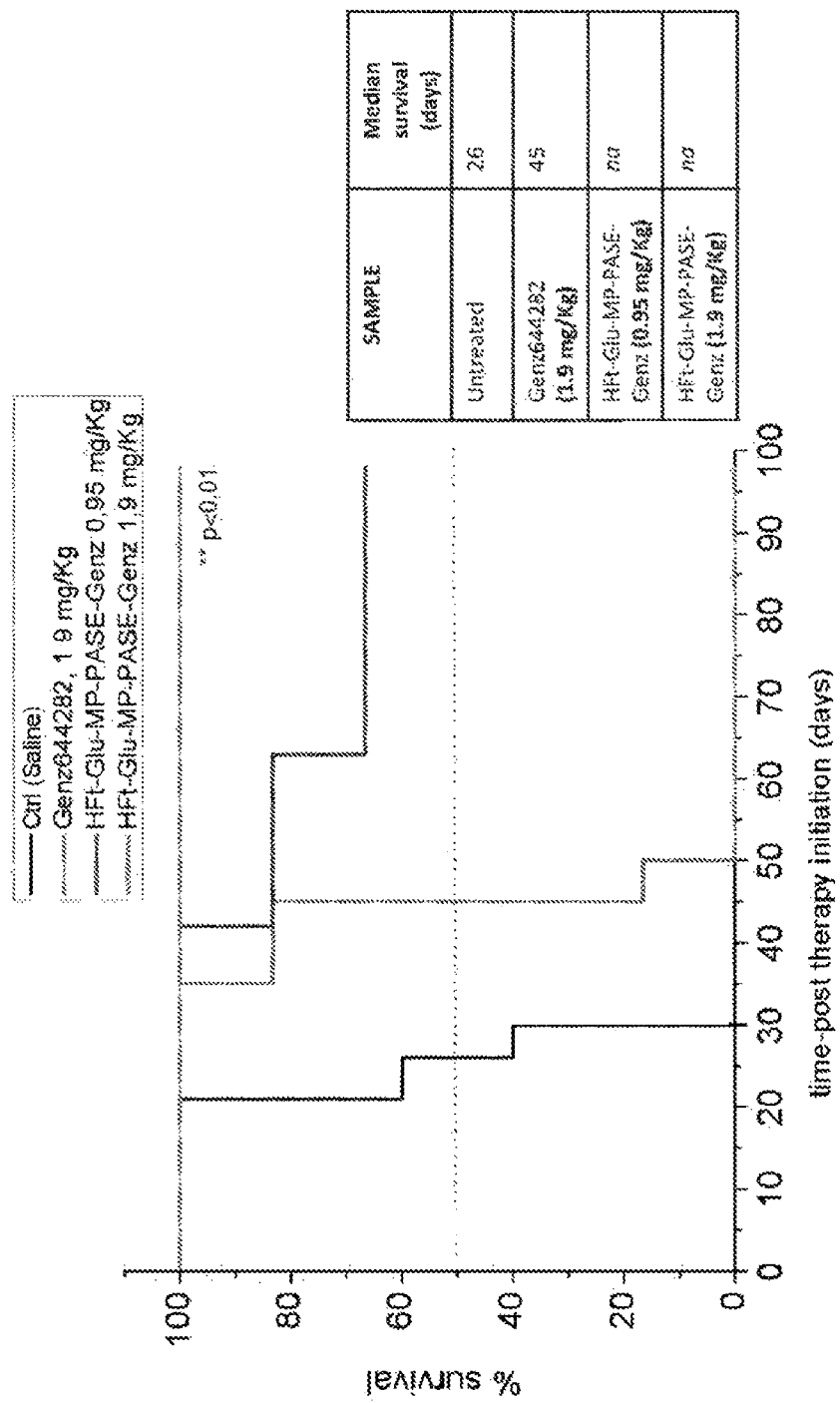
FIG. 16 shows the anti-tumor activity of free Genz 644282™ ([8,9-dimethoxy-5-(2-N-methylaminoethyl)-2,3-methylenedioxy-5H-dibenzo[c,h][1,6]naphthyridin-6-one]) and HFt-Glu-MP-PASE-Genz in pancreatic PaCa44 tumor-bearing mice. Survival curves of different animal groups are shown. Mice were sacrificed when the tumor had reached a volume in the range 1000-1500 mm³.

Five-week-old female CD1 nude mice (Charles River Laboratories, Lecco, Italy) were injected subcutaneously (i.e., right flank) with $4\times10^6$ PaCa-44 cells resuspended in 200 µl of RPMI 1640 medium plus 1% BSA. When tumors had reached a volume of about 100 mm$^3$, mice were randomized in groups of six animals and injected i.v. with 200 µL of physiological saline, Genz 644282™ ([8,9-dimethoxy-5-(2-N-methylaminoethyl)-2,3-methylenedioxy-5H-dibenzo[c,h][1,6]naphthyridin-6-one]) (1.9 mg/Kg) or HFt-Glu-MP-PASE-Genz (0.95 or 1.9 mg/Kg). Mice were injected twice a week for three weeks; tumor volume was measured twice a week with a digital caliper and mouse weight was monitored. When the tumor of mice had reached a volume ≥1500 mm$^3$, animals were sacrificed. In FIG. 15 is reported the tumor growth curves after about two weeks from the last treatment. In this figure is evident the ability of HFt-Glu-MP-PASE-Genz in drastically reducing cancer progression, with a 100% of complete tumor response observed. In FIG. 16 is shown the animal overall survival. All the animals treated with HFt-Glu-MP-PASE-Genz were free of disease and survived after 100 days from the therapy initiation, indicating a great efficacy of the tested compound.

---

The invention claimed is:

1. A fusion protein comprising at least three domains, wherein:
   (a) a first domain comprises the amino acid sequence of the heavy chain of native human ferritin or a variant thereof having at least 90% identity with the amino acid sequence of the heavy chain of native human ferritin (SEQ ID NO:1);
   (b) a second domain comprises the amino acid sequence of a matrix metalloproteinase (MMP) cleavage site; and
   (c) a third amino-terminal domain consists of the amino acid sequence of a polypeptide of at least 20 amino acid residues and which consists essentially of proline, serine and alanine and at least one negatively charged residue selected from glutamate or aspartate (PASE),
   wherein the second domain comprises the amino acid sequence of a matrix metalloproteinase (MMP) cleavage site selected from the group consisting of MMP2, MMP3, MMP7, and MMP9.

2. The fusion protein according to claim 1, wherein said third amino-terminal domain (PASE) has a length which is less than 80 amino acid residues.

3. The fusion protein according to claim 1, wherein the first domain comprises the amino acid sequence of the heavy chain of native human ferritin of SEQ ID NO: 1 or the amino acid sequence of the heavy chain variant of human ferritin of SEQ ID NO: 2.

4. The fusion protein according to claim 1, wherein said third amino-terminal domain (PASE) comprises no more than one glutamate or aspartate within from 15 to 20 residues of the PASE domain.

5. The fusion protein according to claim 1, wherein the proline residues of said third amino-terminal domain (PASE) polypeptide amount to 10-40% of the total amino acid residues thereof.

6. The fusion protein according to claim 1, wherein said third amino-terminal domain (PASE) polypeptide is selected from SEQ ID NO: 9, SEQ ID NO: 10, SEQ ID NO: 11, SEQ ID NO: 12, SEQ ID NO: 13 or SEQ ID NO: 14.

7. The fusion protein according to claim 1, comprising a first and/or second linker amino acid sequence(s) respectively linking the first domain to the second domain and/or the second domain to the third domain, wherein the first and the second amino acid sequences are the same or different from each other.

8. The fusion protein according to claim 1, which is linked to an active ingredient and/or imaging agent.

9. The fusion protein according to claim 1, wherein the heavy chain of the variant human ferritin comprises SEQ ID NO 2, SEQ ID NO 15 or SEQ ID NO 18.

10. A nanoparticle comprising a plurality of monomers of a fusion protein according to claim 1.

11. A nanoparticle according to claim 10 further comprising an active ingredient selected from doxorubicin, mitoxantrone, pixantrone, [8,9-dimethoxy-5-(2-N-methylaminoethyl)-2,3-methylenedioxy-5H-dibenzo[c,h][1,6] naphthyridin-6-one], paclitaxel, auristatins, camptothecins, and gemcitabine, wherein the active ingredient is linked to or encapsulated in said nanoparticle.

12. A pharmaceutical composition comprising a fusion protein according to claim 1, in combination with at least one pharmaceutically acceptable excipient, carrier, or diluent.

13. A pharmaceutical composition comprising the nanoparticles of claim 11, in combination with at least one pharmaceutically acceptable excipient, carrier, or diluent.

* * * * *